(12) United States Patent
Duttagupta et al.

(10) Patent No.: US 9,708,643 B2
(45) Date of Patent: Jul. 18, 2017

(54) CIRCULATING MIRNA BIOMAKER SIGNATURES

(75) Inventors: Radharani Duttagupta, Foster City, CA (US); Keith W. Jones, Sunnyvale, CA (US); Rong Jiang, Pleasanton, CA (US); Robert C. Getts, Collegeville, PA (US); Jeremy N. Gollub, Palo Alto, CA (US)

(73) Assignees: AFFYMETRIX, INC., Santa Clara, CA (US); GENISPHERE, LLC, Hatfield, PA (US)

( * ) Notice: Subject to any disclaimer, the term of this patent is extended or adjusted under 35 U.S.C. 154(b) by 0 days.

(21) Appl. No.: 13/526,463

(22) Filed: Jun. 18, 2012

(65) Prior Publication Data
US 2013/0012405 A1 Jan. 10, 2013

Related U.S. Application Data

(60) Provisional application No. 61/498,527, filed on Jun. 17, 2011.

(51) Int. Cl.
*C12Q 1/68* (2006.01)

(52) U.S. Cl.
CPC .......... *C12Q 1/6806* (2013.01); *C12Q 1/6879* (2013.01); *C12Q 1/6886* (2013.01); *C12Q 2600/158* (2013.01); *C12Q 2600/178* (2013.01)

(58) Field of Classification Search
CPC ................................................. C12Q 2523/32
See application file for complete search history.

(56) References Cited

U.S. PATENT DOCUMENTS

| | | | | |
|---|---|---|---|---|
| 5,071,570 A | * | 12/1991 | Shiraki et al. | 210/774 |
| 2006/0204989 A1 | * | 9/2006 | Kopreski | 435/6 |
| 2009/0291438 A1 | * | 11/2009 | Kopreski | 435/6 |
| 2011/0144914 A1 | * | 6/2011 | Harrington | C12Q 1/6883 702/19 |
| 2011/0262914 A1 | * | 10/2011 | Wohlgemuth et al. | 435/6.11 |

OTHER PUBLICATIONS

Turchinovich et al ("Characterization of extracellular circulating microRNA" NAR: 2011, pp. 1-11).*
Wang et al in "Yeast tRNA as Carrier in the Isolation of Microscale RNA for Global Amplication and Expression Profiling" (Biotechniques 2002: vol. 33, No. 4, pp. 788-796).*
Buermans et al. New methods for next generation sequencing based microRNA expression profiling. (2010) BMC Genomics 11: 716.
Chamnongpol et al. A Rapid, Quantitative Assay for Direct Detection of MicroRNAs and Other Small RNAs Using Splinted Ligation. (2010) Methods Mol Biol 667: 3-17.
Chen et al. Characterization of microRNAs in serum: a novel class of biomarkers for diagnosis of cancer and other diseases. (2008) Cell Res 18: 997-1006.
Chiu et al. Effects of Blood-Processing Protocols on Fetal and Total DNA Quantification in Maternal Plasma. (2001) Clin Chem 47: 1607-1613.
Duttagupta et al. Genome-Wide Maps of Circulating miRNA Biomarkers for Ulcerative Colitis. (2012) Plos One vol. 7(2): e31241.
Duttagupta et al. Impact of Cellular miRNAs on Circulating miRNA Biomarker Signatures. (2011) Plos One vol. 6:6 e20769.
Gaillard and Strauss. Ethanol precipitation of DNA with linear polyacrylamide as carrier. (1990) Nucleic Acids Research 18: 378.
Garzon et al. (2009). MicroRNAs in Cancer. Annu Rev Med 60: 167-179.
Hsu et al. miRNAMap 2.0: genomic maps of microRNAs in metazoan genomes. (2008) Nucleic Acids Res 36: D165-169.
Hunter et al. Detection of microRNA Expression in Human Peripheral Blood Microvesicles. (2008). Plos One 3: e3694.
Kong et al. Strategies for Profiling MicroRNA Expression. (2009) J Cell Physiol 218(1): 22-25.
Kosaka et al. Circulating microRNA in body fluid: a new potential biomarker for cancer diagnosis and prognosis. (2010). Cancer Sci 101: 2087-2092.
Landgraf et al. A Mammalian microRNA Expression Atlas Based on Small RNA Library Sequencing. (2007) Cell 129: 1401-1414.
Lee et al. Systematic evaluation of microRNA processing patterns in tissues, cell lines, and tumors. (2008) RNA 14: 35-42.
Lui et al. Patterns of Known and Novel Small RNAs in Human Cervical Cancer. (2007) Cancer Res 67: (13) 6031-6043.
Mitchell et al. Circulating microRNAs as stable blood-based markers for cancer detection. (2008) Proc Natl Acad Sci USA 105: 10513-10518.
Reid et al. Circulating microRNAs: Association with disease and potential use as biomarkers. (2011). Crit rev Oncol Hematol, Nov; 80(2): 193-208, EPub Dec. 8, 2010.
Storey et al. Statistical significance for genomewide studies. (2003). Proc Natl Acad Sci USA 100: 9440-9445.
Tanaka et al. Down-Regulation of miR-92 in Human Plasma is a Novel Marker for Acute Leukemia Patients. (2009) Plos One 4: e5532.
Wang. RNA amplification for successful gene profiling analysis. (2005) J Transl Med. 25(3):28.
Zhang et al. Gene set enrichment analyses revealed differences in gene expression patterns between males and females. (2009) In Silico Biol 9: 55-63.

* cited by examiner

*Primary Examiner* — Catherine S Hibbert

(57) ABSTRACT

Methods for diagnosis and surveillance of complex multifactorial disorders such as cancer by screening of easily accessible biomarkers are disclosed. Highly stable cell free Circulating Nucleic Acids (CNA) present as both RNA and DNA species have been discovered in the blood and plasma of humans. Correlations between tumor-associated genomic/epigenetic/transcriptional changes and alterations in CNA levels are strong predictors of the utility of this biomarker class as clinical indicators. Methods for using microRNAs (miRNAs) representing a class of naturally occurring small non-coding RNAs of 19-25 nt as markers that can associate their specific expression profiles with cancer development are disclosed. Methods for isolating plasma fractions for the study of miRNA biomarkers and for measurement of circulating miRNA levels are disclosed.

10 Claims, 12 Drawing Sheets

Figure 2.
2A.
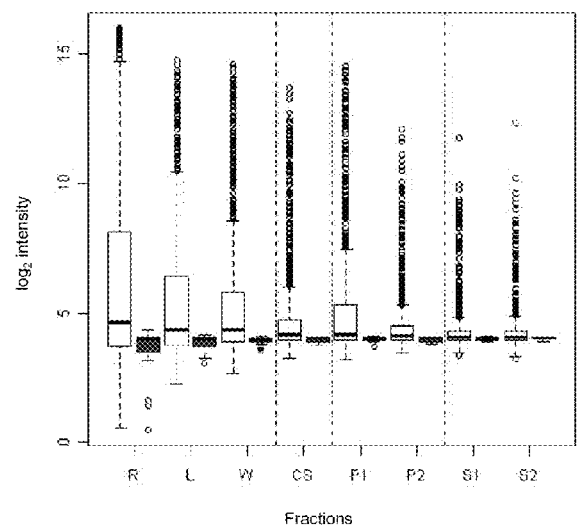
2B.
2C.
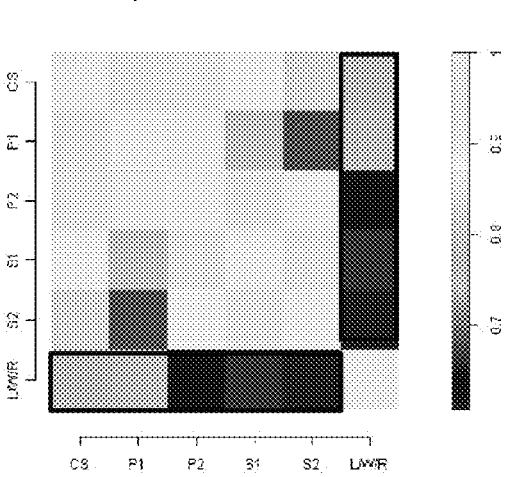

Figure 4.
4A.
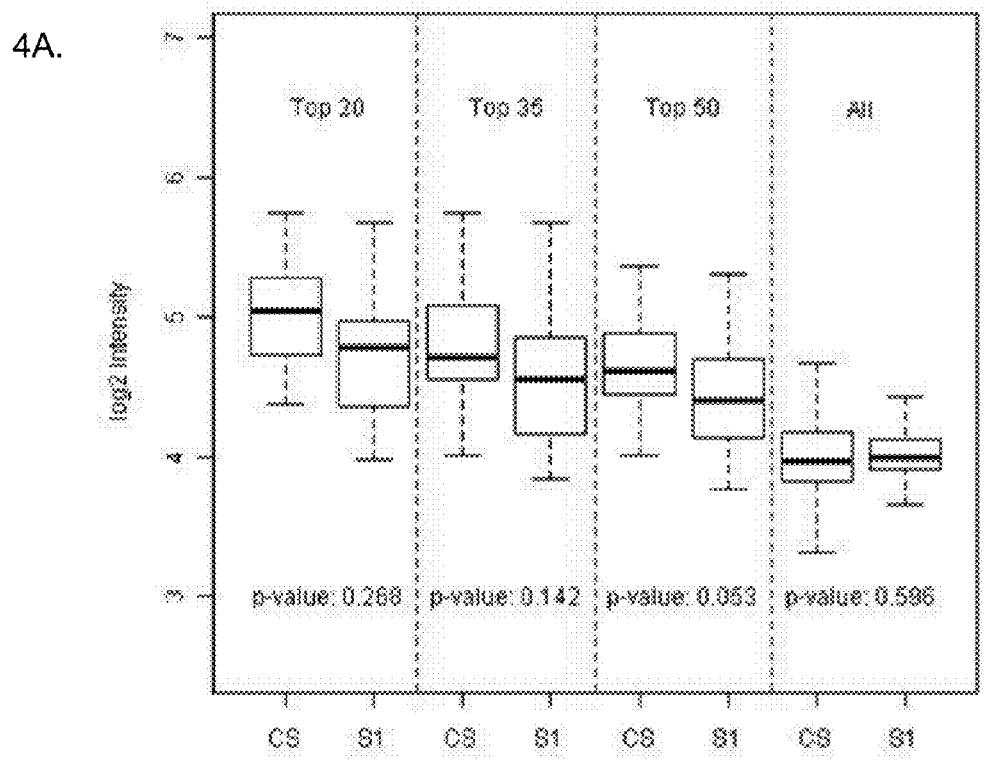
4B.
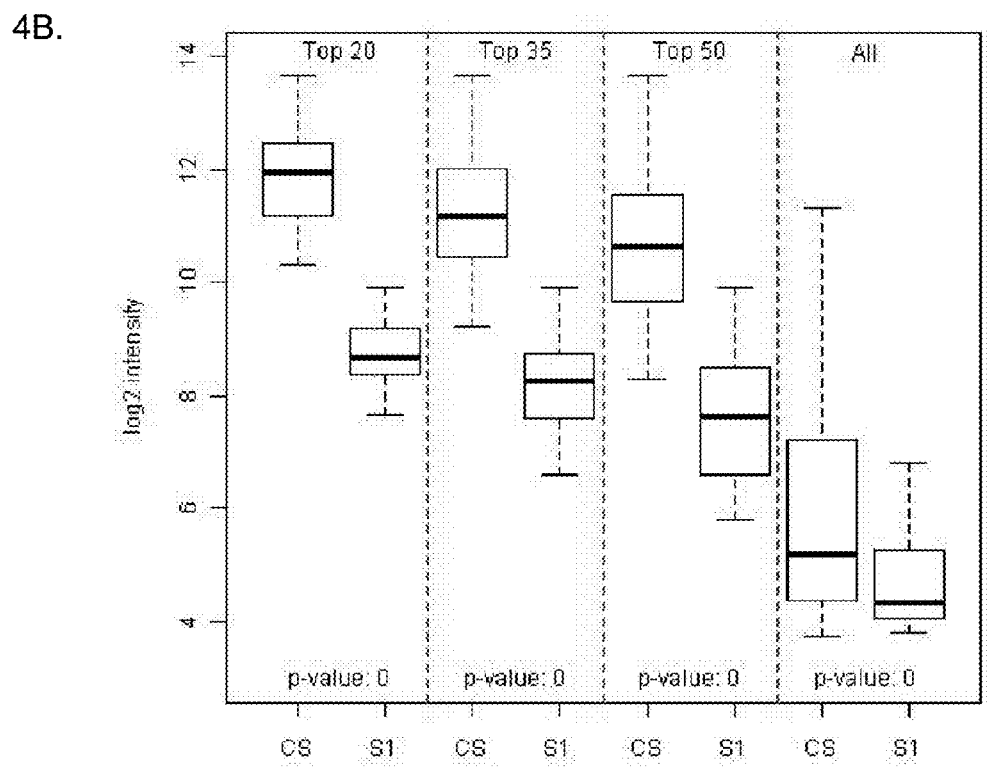

Fig. 8

| differentially expressed miRNAs | Chromosome and location | Genomic Classification | Expression Data * | Score | Fold Change (Females/Males) | q-value | Target genes # |
|---|---|---|---|---|---|---|---|
| hsa-miR-548a-3p | Chr 6:135601991-135602087 (+) Chr 6:18679994-18680090 (+) Chr 8:105565773-105565869 (-) | intergenic | no data | 3.200695 | 1.942375494 | 0 | DAPK1 |
| hsa-miR-1323 | Chr 19:58867034-58867106 (+) | intergenic | nodata | 2.653858 | 1.940674517 | 0 | DAPK1 |
| hsa-miR-940 | Chr 16:2261749-2261842 (+) | intergenic | cervix | 2.4019115 | 1.762450911 | 0 | E2F1 |
| hsa-miR-1292 | Chr 20:2581423-2581488 (+) | intronic | nodata | 2.2228335 | 1.632659454 | 0 | TIMM50 |

*Expression data from (a) mirbase (http://www.mirbase.org/) (b) miRNAorg (http://www.microrna.org) and ©miRNAMap (http://mirnamap.mbc.nctu.edu.tw). # Target genes from Breast Cancer Database (http://www.itb.cnr.it/breastcancer/)

CIRCULATING MIRNA BIOMAKER SIGNATURES

RELATED APPLICATIONS

This application claims priority to U.S. Provisional application No. 61/498,527, filed Jun. 17, 2011, the disclosure of which is incorporated herein by reference in its entirety for all purposes.

FIELD OF THE INVENTION

The present invention is generally in the field of nucleic acid analysis.

BACKGROUND OF THE INVENTION

Effective diagnosis and surveillance of complex multifactorial disorders such as cancer can be improved by screening of easily accessible biomarkers. Highly stable cell free Circulating Nucleic Acids (CNA) present as both RNA and DNA species have been discovered in the blood and plasma of humans. Correlations between tumor-associated genomic/epigenetic/transcriptional changes and alterations in CNA levels are strong predictors of the utility of this biomarker class as promising clinical indicators. Towards this goal microRNAs (miRNAs) representing a class of naturally occurring small non-coding RNAs of 19-25 nt in length have emerged as an important set of markers that can associate their specific expression profiles with cancer development. In this study we investigate some of the pre-analytic considerations for isolating plasma fractions for the study of miRNA biomarkers. We find that measurement of circulating miRNA levels are frequently confounded by varying levels of cellular miRNAs of different hematopoietic origins. In order to assess the relative proportions of this cell-derived class, we have fractionated whole blood into plasma and its ensuing sub-fractions. Cellular miRNA signatures in cohorts of normal individuals are catalogued and the abundance and gender specific expression of bona fide circulating markers explored after calibrating the signal for this interfering class. A map of differentially expressed profiles is presented and the intrinsic variability of circulating miRNA species investigated in subsets of healthy males and females.

A considerable proportion of the animal genome representing both DNA and coding/non-coding RNAs can be detected in circulation. Identified first in 1948 and thought to originate as products of apoptosis or active release from cells, extracellular circulating DNA fragments ranging in size between 500 bp to greater than 30 Kb have been characterized both in normal and diseased individuals (see, Fleischhacker and Schmidt (2007) Biochim Biophys Acta 1775: 181-232 and van der Vaart and Pretorius P J (2007) Clin Chem 53: 2215). Although the physiological functions of these circulating species are unclear, the presence of tumor associated genetic alterations in these molecules combined with inherent molecular stability makes them attractive substrates for disease detection, tracking and prediction. Of the various classes of circulating nucleic acids— miRNAs representing approximately 1-2% of the known genes in eukaryotes (see John et al. (2004) PLoS Biol 2: e363) and characterized by highly conserved small non-coding RNAs of 19-25 nt in length are particularly attractive candidates. Approximately 940 mature miRNAs have been characterized to date in humans (see, Griffiths-Jones (2004) Nucleic Acids Res 32: D109-111, Griffiths-Jones et al. (2006) Nucleic Acids Res 34: D140-144 and Griffiths-Jones et al. (2008) Nucleic Acids Res 36: D154-158) and it is believed that approximately 30% of all annotated human genes may potentially be targeted by miRNAs through post-transcriptional mechanisms (see, Lewis et al. (2005) Cell 120: 15-20).

The number of targets is likely to increase when taking into account widespread unannotated transcription (see, Willingham and Gingeras (2006) Cell 125: 1215-1220) thus making these molecules a powerful regulatory class with the potential to intercept a wide network of fundamental cellular processes. Over the past several years an increasing number of miRNAs have been implicated in cancer development with mechanisms ranging from copy number alterations/ mutations/epigenetic silencing or dysregulated transcriptional control of miRNA loci (see, Esquela-Kerscher and Slack (2006) Nat Rev Cancer 6: 259-269 and Garzon R, Cahn G A and Croce C M (2009) MicroRNAs in Cancer. Annu Rev Med 60: 167-179.)

These data reveal the oncogenic and tumor suppressive nature of miRNAs and highlight the correlation between various cancers and differential miRNA signatures. The ability to profile miRNAs in circulation thus represents a non-invasive opportunity to investigate disease specific miRNAs and is a promising alternative approach to current strategies for cancer surveillance.

A critical prerequisite for developing circulating miRNA-based diagnostics is the ability to accurately isolate and measure representative miRNA species in biofluids. In spite of high concentration of RNAses in plasma and serum, circulating miRNAs are surprisingly tractable. A key molecular property of these species is that they are highly stable in circulation and can survive unfavorable physiological conditions such as extreme variations in pH and multiple freeze thaw cycles (see Chen et al. (2008) Cell Res 18: 997-1006 and Mitchell et al. (2008) Proc Natl Acad Sci USA 105: 10513-10518).

Circulating miRNA may also be tumor derived, thus directly reflecting disease burden and are protected from degradation though inclusion in RNA binding proteins (see Wang et al. (2010) Nucleic Acids Res 38: 7248-7259) or sub-cellular particles (see Kosaka et al. (2010) Cancer Sci 101: 2087-2092 and Wang et al. (2010) Nucleic Acids Res 38: 7248-7259 and Valadi et al. (2007) Nat Cell Biol 9: 654-659) distinct from the hematopoietic cellular population.

All of these cellular attributes are susceptible to a variety of pre-analytic factors involving sample collection, processing, storage and extraction methods that can determine both the quantitative and qualitative effectiveness of this species for clinical use. In an effort to standardize results and bring uniformity to data quality several studies over the past few years have begun to explore and put forward recommendations for a subset of these pre-analytical variables (see Chen et al. (2008) Cell Res 18: 997-1006, Mitchell et al. (2008) Proc Natl Acad Sci USA 105: 10513-10518 and Chiu et al. (2001) Clin Chem 47: 1607-1613).

SUMMARY OF THE INVENTION

Methods for sample extraction are disclosed herein. In some aspects the disclosed methods optimize the integrity and detection of cell-free RNA while minimizing the presence of interfering cellular miRNAs. The methods may be used in the analysis of inter-individual variability in normal cohorts of male and female individuals, for example. The methods can be used to generate maps of circulating miRNAs following a step of extracting out interfering signals from contaminant cells.

In another aspect, gender specific signatures in the profiles of male and female individuals are disclosed.

The methods may be used to analyze cellular miRNA signatures as a variable useful for interpreting the complexity of circulating miRNA profiles.

BRIEF DESCRIPTION OF THE DRAWINGS

FIG. 2A shows box plots profiling of blood derived fractions and correlation of miRNA intensities between individual fractions and contaminant classes. (A)

FIG. 2B shows counts of detected features in Leukocytes (L), WBC (W) and RBC (R) constituting the contaminant profile.

FIG. 2C shows a heat map of Spearman's Rank Correlation coefficients of the highest expressing 100 miRNAs across all 5 plasma fractions (CS, S1, S2, P1 and P2). The contaminant class is designated as LWR and represents 313 miRNAs derived from the union of the Leukocytes, WBC and RBC fractions. Correlation values are shown in the bar scale.

FIG. 4A shows intensity distributions from the highest expressed 20, 35, 50 or all 534 human miRNAs in the CS and S1 fractions after removal of contaminant features. P-values from paired Student's t-tests, contrasting the intensities for each pair of conditions are reported.

FIG. 4B shows intensity distributions from the highest expressed 20, 35, 50 or all 313 contaminant miRNAs in the CS and S1 fractions with p-values from paired t-tests measuring significance.

FIG. 8 shows statistically significantly differentially expressed miRNA features in females compared to males based on SAM analysis. The "Score" represents the modified t-test statistics calculated by SAM. The "Fold Change" denotes the ratios of the mean intensity in female samples over male samples. shows Box plot of signal intensity distribution of human miRNAs (white) and background probes (red) for 8 males and 10 females after background subtraction, quantile normalization and median summarization.

DETAILED DESCRIPTION OF THE INVENTION

Figure 1:
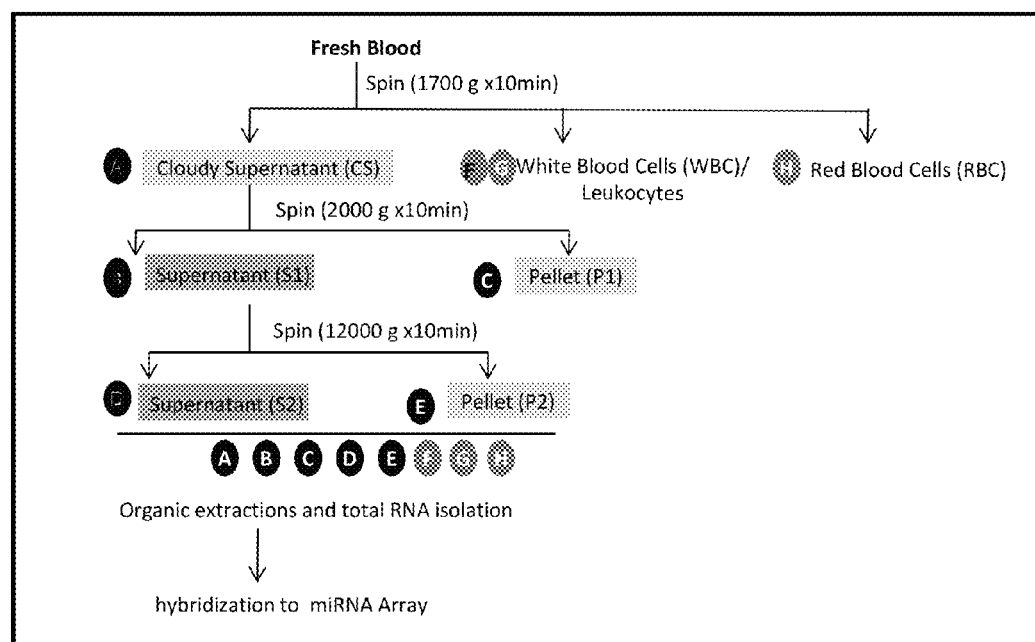
FIG. 1 shows the fractionation workflow. Separation of whole blood into distinct fractions: WBC, RBC, Leukocytes and CS, S1, S2, P1, P2 through differential centrifugation. Total RNA was extracted from each fraction and hybridized to miRNA arrays.

Reference will now be made in detail to exemplary embodiments of the invention. While the invention will be described in conjunction with the exemplary embodiments, it will be understood that they are not intended to limit the invention to these embodiments. On the contrary, the invention is intended to cover alternatives, modifications and equivalents, which may be included within the spirit and scope of the invention.

The invention has many preferred embodiments and relies on many patents, applications and other references for details known to those of the art. Therefore, when a patent, application, or other reference, such as a printed publication, is cited or repeated below, it should be understood that it is incorporated by reference in its entirety for all purposes and particularly for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being, but may also be other organisms including, but not limited to, mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series (Vols. I-IV), Using Antibodies: A Laboratory Manual, Cells: A Laboratory Manual, PCR Primer: A Laboratory Manual,* and Molecular *Cloning: A Laboratory Manual* (all from Cold Spring Harbor Laboratory Press), Gait, *"Oligonucleotide Synthesis: A Practical Approach"* 1984, *IRL Press, London,* Nelson and Cox (2000), Lehninger et al., (2008) *Principles of Biochemistry* 5th Ed., W.H. Freeman Pub., New York, N.Y. and Berg et al. (2006) *Biochemistry, 6$^{th}$ Ed.,* W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Patent Pub. No. 20050074787, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Publication No. WO 99/36760 and WO 01/58593, which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques may be applied to polypeptide arrays.

The present invention also contemplates many uses for polymers attached to solid substrates. These uses include gene expression monitoring, transcript profiling, library screening, genotyping, epigenetic analysis, methylation pattern analysis, tumor typing, pharmacogenomics, agrigenetics, pathogen profiling and detection and diagnostics. Gene expression monitoring and profiling methods can be shown in U.S. Pat. Nos. 5,800,992, 6,013,449, 6,020,135, 6,033, 860, 6,040,138, 6,177,248 and 6,309,822. Genotyping and uses therefore are shown in U.S. Patent Publication Nos. 20030036069 and 20070065816 and U.S. Pat. Nos. 5,856, 092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain embodiments. Prior to or concurrent with analysis, the sample may be amplified by a variety of mechanisms. In some aspects nucleic acid amplification methods such as PCR may be combined with the disclosed methods and systems. See, for example, *PCR Technology: Principles and Applications for DNA Amplification* (Ed. N. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); PCR (Eds. McPherson et al., IRL Press, Oxford); and U.S. Pat. Nos. 4,683,202, 4,683,195, 4,800,159, 4,965,188, and 5,333,675, each of which is incorporated herein by reference in their entireties for all purposes. Enzymes and related methods of use in molecular biology that may be used in combination with the disclosed methods and systems are reviewed, for example, in Rittie and Perbal, *J. Cell Commun. Signal.* (2008) 2:25-45. The sample may be amplified on the array. See, for example, U.S. Pat. No. 6,300,070 and which is incorporated herein by reference in its entirety for all purposes.

Methods for labeling microRNAs and other small RNAs are disclosed, for example, in Chamnongpol et al. Methods Mol Biol 2010:667:3-17. Other methods are described in Kong et al. J Cell Physiol 2009 218(1):22-5. Expression profiling of mircorRNAs may be performed using array technology, sequencing technology (see Buermans et al. BMC Genomics 2010 11:716. or any method available. Each of these references is incorporated by reference in its entirety for all purposes.

Effective diagnosis and surveillance of complex multifactorial disorders such as cancer can be improved by screening of easily accessible biomarkers. Highly stable cell free Circulating Nucleic Acids (CNA) present as both RNA and DNA species have been discovered in the blood and plasma of humans. Correlations between tumor-associated genomic/epigenetic/transcriptional changes and alterations in CNA levels are strong predictors of the utility of this biomarker class as promising clinical indicators. Towards this goal microRNAs (miRNAs) representing a class of naturally occurring small non-coding RNAs of 19-25 nt in length have emerged as an important set of markers that can associate their specific expression profiles with cancer development. In this study we investigate some of the pre-analytic considerations for isolating plasma fractions for the study of miRNA biomarkers. We find that measurement of circulating miRNA levels are frequently confounded by varying levels of cellular miRNAs of different hematopoietic origins. In order to assess the relative proportions of this cell-derived class, we have fractionated whole blood into plasma and its ensuing sub-fractions. Cellular miRNA signatures in cohorts of normal individuals are catalogued and the abundance and gender specific expression of bona fide circulating markers explored after calibrating the signal for this interfering class. A map of differentially expressed profiles is presented and the intrinsic variability of circulating miRNA species investigated in subsets of healthy males and females.

Although the invention is described in conjunction with the exemplary embodiments, the invention is not limited to these embodiments. On the contrary, the invention encompasses alternatives, modifications and equivalents, which may be included within the spirit and scope of the invention. The invention has many embodiments and relies on many patents, applications and other references for details known to those of the art. Therefore, when a patent, application, or other reference is cited or repeated below, the entire disclosure of the document cited is incorporated by reference in its entirety for all purposes as well as for the proposition that is recited. All documents, i.e., publications and patent applications, cited in this disclosure, including the foregoing, are incorporated herein by reference in their entireties for all purposes to the same extent as if each of the individual documents were specifically and individually indicated to be so incorporated herein by reference in its entirety. The methods disclosed herein are related to Duttagupta et al. PLos One (2011) vol 6:6 e20769 and Duttagupta et al. PLoS One (2012) vol 7(2):e31241, both of which are incorporated herein by reference in their entireties for all purposes.

As used in this application, the singular form "a," "an," and "the" include plural references unless the context clearly dictates otherwise. For example, the term "an agent" includes a plurality of agents, including mixtures thereof.

Throughout this disclosure, various aspects can be presented in a range format. When a description is provided in range format, this is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

The disclosed methods, kits and compositions may employ arrays of probes on solid substrates in some embodiments. Methods and techniques applicable to polymer (including nucleic acid and protein) array synthesis have been described in, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, and in WO 99/36760 and WO 01/58593, which are all incorporated herein by reference in their entirety for all purposes. Patents that describe synthesis techniques include U.S. Pat. Nos. 5,412,087, 6,147,205, 6,262,216, 6,310,189, 5,889,165, and 5,959,098. Nucleic acid probe arrays are described in many of the above patents, but the same techniques may be applied to polypeptide probe arrays.

Nucleic acid arrays that are useful include, but are not limited to, those that are commercially available from Affymetrix (Santa Clara, Calif.) under the brand name GENECHIP® array. Example arrays are shown on the website at the Affymetrix web site.

Probe arrays have many uses including, but are not limited to, gene expression monitoring, profiling, library screening, genotyping and diagnostics. Methods of gene expression monitoring and profiling are described in U.S. Pat. Nos. 5,800,992, 6,013,449, 6,020,135, 6,033,860, 6,040,138, 6,177,248 and 6,309,822. Genotyping methods, and uses thereof, are disclosed in U.S. patent application Ser. No. 10/442,021 (abandoned) and U.S. Pat. Nos. 5,856,092, 6,300,063, 5,858,659, 6,284,460, 6,361,947, 6,368,799, 6,333,179, and 6,872,529. Other uses are described in U.S. Pat. Nos. 5,871,928, 5,902,723, 6,045,996, 5,541,061, and 6,197,506.

Feature refers to a localized area on a solid support that is, or was, intended to be used for formation of a selected molecule and is otherwise referred to herein in the alternative as a selected or predefined region. The predefined region may have any convenient shape, e.g., circular, rectangular, elliptical, wedge-shaped, etc. For the sake of brevity herein, "features" are sometimes referred to simply as "regions" or "known locations." In some embodiments, a feature, and therefore the area upon which each distinct compound or group of compounds is synthesized, can be as small as or smaller than 1 micron square as shown in the patents cited above, but is often about 5 microns by 5 microns. Within these regions, the molecule synthesized therein is preferably synthesized in a substantially pure form.

"Solid support", "support", and "substrate" refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See the above patents for a broader list of supports.

A "protective group" is a moiety which is bound to a molecule and which may be spatially removed upon selective exposure to an activator such as electromagnetic radiation. Several examples of protective groups are known in the literature and will become evident upon further reading of the present disclosure. Other examples of activators include ion beams, electric fields, magnetic fields, electron beams, x-ray, and the like.

Samples can be processed by various methods before analysis. Prior to, or concurrent with, analysis a nucleic acid sample may be amplified by a variety of mechanisms, some of which may employ PCR. (See, for example, *PCR Technology: Principles and Applications for DNA Amplification*, Ed. N. A. Erlich, Freeman Press, NY, N.Y., 1992; *PCR Protocols: A Guide to Methods and Applications*, Eds. Innis, et al., Academic Press, San Diego, Calif., 1990; Mattila et al., *Nucleic Acids Res.*, 19:4967, 1991; Eckert et al., *PCR Methods and Applications*, 1:17, 1991; PCR, Eds. McPherson et al., IRL Press, Oxford, 1991; and U.S. Pat. Nos. 4,683,202, 4,683,195, 4,800,159 4,965,188, and 5,333,675, each of which is incorporated herein by reference in their entireties for all purposes. The sample may also be amplified on the probe array. (See, for example, U.S. Pat. No. 6,300,070 and U.S. patent application Ser. No. 09/513,300 (abandoned), all of which are incorporated herein by reference).

Other suitable amplification methods include the ligase chain reaction (LCR) (see, for example, Wu and Wallace, *Genomics*, 4:560 (1989), Landegren et al., *Science*, 241:1077 (1988) and Barringer et al., *Gene*, 89:117 (1990)), transcription amplification (Kwoh et al., *Proc. Natl. Acad. Sci. USA*, 86:1173 (1989) and WO 88/10315), self-sustained sequence replication (Guatelli et al., *Proc. Nat. Acad. Sci. USA*, 87:1874 (1990) and WO 90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909 and 5,861,245) rolling circle amplification (RCA) (for example, Fire and Xu, *PNAS* 92:4641 (1995) and Liu et al., *J. Am. Chem. Soc.* 118:1587 (1996)) and nucleic acid based sequence amplification (NABSA). (See also, U.S. Pat. Nos. 5,409,818, 5,554,517, and 6,063,603, each of which is incorporated herein by reference). Other amplification methods that may be used are described in, for instance, U.S. Pat. Nos. 6,582,938, 5,242,794, 5,494,810, and 4,988,617, each of which is incorporated herein by reference.

Other amplification methods that may be used are described in, U.S. Pat. Nos. 5,242,794, 5,494,810, 4,988,617 and in U.S. Ser. No. 09/854,317. Other amplification methods are also disclosed in Dahl et al., *Nuc. Acids Res.* 33(8):e71 (2005) and circle to circle amplification (C2CA) Dahl et al., *PNAS* 101:4548 (2004). Locus specific amplification and representative genome amplification methods may also be used. US Patent Pub. No. 20090117573 discloses methods for multiplex amplification of targets using arrayed probes.

Additional methods of sample preparation and techniques for reducing the complexity of a nucleic sample are described in Dong et al., *Genome Research*, 11:1418 (2001), U.S. Pat. Nos. 6,361,947, 6,391,592, 6,632,611, 6,872,529 and 6,958,225, and in U.S. patent application Ser. No. 09/916,135 (abandoned).

Hybridization assay procedures and conditions vary depending on the application and are selected in accordance with known general binding methods, including those referred to in Maniatis et al., *Molecular Cloning: A Laboratory Manual*, $2^{nd}$ Ed., Cold Spring Harbor, N.Y., (1989); Berger and Kimmel, *Methods in Enzymology, Guide to Molecular Cloning Techniques*, Vol. 152, Academic Press, Inc., San Diego, Calif. (1987); Young and Davism, *Proc. Nat'l. Acad. Sci.*, 80:1194 (1983). Methods and apparatus for performing repeated and controlled hybridization reactions have been described in, for example, U.S. Pat. Nos. 5,871,928, 5,874,219, 6,045,996, 6,386,749, and 6,391,623 each of which are incorporated herein by reference.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than about 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations or conditions of 100 mM MES, 1 M [Na+], 20 mM EDTA, 0.01% Tween-20 and a temperature of 30-50° C., or at about 45-50° C. Hybridizations may be performed in the presence of agents such as herring sperm DNA at about 0.1 mg/ml, acetylated BSA at about 0.5 mg/ml. As other factors may affect the stringency of hybridization, including base composition and length of the complementary strands, presence of organic solvents and extent of base mismatching, the combination of parameters is more important than the absolute measure of any one alone. Hybridization conditions suitable for microarrays are described in the Gene Expression Technical Manual, 2004 and the GENECHIP® Mapping Assay Manual, 2004.

Hybridization signals can be detected by conventional methods, such as described by, e.g., U.S. Pat. Nos. 5,143,854, 5,578,832, 5,631,734, 5,834,758, 5,936,324, 5,981,956, 6,025,601, 6,141,096, 6,185,030, 6,201,639, 6,218,803, and 6,225,625, U.S. patent application Ser. No. 10/389,194 (U.S. Patent Application Publication No. 2004/0012676, allowed on Nov. 9, 2009) and PCT Application PCT/US99/06097 (published as WO 99/47964), each of which is hereby incorporated by reference in its entirety for all purposes).

The practice of the methods may also employ conventional biology methods, software and systems. Computer software products of the invention typically include, for instance, computer readable medium having computer-executable instructions for performing the logic steps of the method of the invention. Suitable computer readable medium include, for example a floppy disk, CD-ROM/DVD/DVD-ROM, hard-disk drive, flash memory, ROM/RAM, and magnetic tapes. The computer executable instructions may be written in a suitable computer language or combination of several computer languages. Basic computational biology methods which may be employed in the methods are described in, for example, Setubal and Meidanis et al., *Introduction to Computational Biology Methods*, PWS Publishing Company, Boston, (1997); Salzberg, Searles, Kasif, (Ed.), *Computational Methods in Molecular Biology*, Elsevier, Amsterdam, (1998); Rashidi and Buehler, *Bioinformatics Basics: Application in Biological Science and Medicine*, CRC Press, London, (2000); and Ouelette and Bzevanis *Bioinformatics: A Practical Guide for Analysis of Gene and Proteins*, Wiley & Sons, Inc., $2^{nd}$ ed., (2001). (See also, U.S. Pat. No. 6,420,108).

The invention may also make use of various computer program products and software for a variety of purposes, such as probe design, management of data, analysis, and instrument operation. (See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170).

Genetic information obtained can be transferred over networks such as the internet, as disclosed in, for instance, (U.S. Patent Application Publication No. 20030097222), U.S. Patent Application Publication No. 20020183936, abandoned), U.S. Patent Application Publication No. 20030100995, U.S. Patent Application Publication No. 20030120432, Ser. No. 10/328,818 U.S. Patent Application Publication No. 20040002818, U.S. Patent Application Publication No. 20040126840, abandoned), Ser. No. 10/423,403 (U.S. Patent Application Publication No. 20040049354.

Methods for multiplex amplification and analysis of nucleic acids have been disclosed, for example in U.S. Pat. Nos. 6,858,412 and 7,700,323. Related methods are also disclosed in U.S. Pat. Nos. 6,558,928, 6,235,472, 6,221,603, 5,866,337, and 4,988,617. Applications of MIP technology have been described in, for example, Daly et al. *Clin Chem* 2007, 53(7): 1222-1230, Dumaual, et al. *Pharmacogenomics* 2007, 8(3):293-305, Ireland et al., *Hum Genet.* 2006, 119:75-83, Moorhead et al. *Eur. J. Hum Genet.* 2006, 14:207-215, Hardenbol, et al., *Genome Res.* 2005, 15:269-275 and Hardenbol, et al. *Nat. Biotech.* 2003, 21:673-678 and Wang et al. *NAR* 33:e183.

Many of the methods and systems disclosed herein utilize enzyme activities. A variety of enzymes are well known, have been characterized and many are commercially available from one or more supplier. For a review of enzyme activities commonly used in molecular biology see, for example, Rittie and Perbal, *J. Cell Commun. Signal.* (2008) 2:25-45, incorporated herein by reference in its entirety. Exemplary enzymes include DNA dependent DNA polymerases (such as those shown in Table 1 of Rittie and Perbal), RNA dependent DNA polymerase (see Table 2 of Rittie and Perbal), RNA polymerases, ligases (see Table 3 of Rittie and Perbal), enzymes for phosphate transfer and removal (see Table 4 of Rittie and Perbal), nucleases (see Table 5 of Rittie and Perbal), and methylases.

The term "Strand Displacement Amplification" (SDA) is an isothermal in vitro method for amplification of nucleic acid. In general, SDA methods initiate synthesis of a copy of a nucleic acid at a free 3' OH that may be provided, for example, by a primer that is hybridized to the template. The DNA polymerase extends from the free 3' OH and in so doing, displaces the strand that is hybridized to the template leaving a newly synthesized strand in its place. Subsequent rounds of amplification can be primed by a new primer that hybridizes 5' of the original primer or by introduction of a nick in the original primer. Repeated nicking and extension with continuous displacement of new DNA strands results in exponential amplification of the original template. Methods of SDA have been previously disclosed, including use of nicking by a restriction enzyme where the template strand is resistant to cleavage as a result of hemimethylation. Another method of performing SDA involves the use of "nicking" restriction enzymes that are modified to cleave only one strand at the enzymes recognition site. A number of nicking restriction enzymes are commercially available from New England Biolabs and other commercial vendors.

Polymerases useful for SDA generally will initiate 5' to 3' polymerization at a nick site, will have strand displacing activity, and preferably will lack substantial 5' to 3' exonuclease activity. Enzymes that may be used include, for example, the Klenow fragment of DNA polymerase I, Bst polymerase large fragment, Phi29, and others. DNA Polymerase I Large (Klenow) Fragment consists of a single polypeptide chain (68 kDa) that lacks the 5' to 3' exonuclease activity of intact E. coli DNA polymerase I. However, DNA Polymerase I Large (Klenow) Fragment retains its 5' to 3' polymerase, 3' to 5' exonuclease and strand displacement activities. The Klenow fragment has been used for SDA. For methods of using Klenow for SDA see, for example, U.S. Pat. Nos. 6,379,888; 6,054,279; 5,919,630; 5,856,145; 5,846,726; 5,800,989; 5,766,852; 5,744,311; 5,736,365; 5,712,124; 5,702,926; 5,648,211; 5,641,633; 5,624,825; 5,593,867; 5,561,044; 5,550,025; 5,547,861; 5,536,649; 5,470,723; 5,455,166; 5,422,252; 5,270,184, the disclosures of which are incorporated herein by reference. There are many thermostable polymerases and polymerase mixtures that are commercially available and may be used in combination with the disclosed methods.

Circulating Nucleic Acids.

Methods for exploring the contribution of cellular miRNAs of hematopoietic origin in the isolation and analysis of cell-free circulating miRNAs are disclosed herein. Considerable proportions of miRNAs derived from Red and White Blood Cells (RBCs and WBCs), are present as contaminants in plasma preparations with the potential to mask the intensities of truly circulating miRNA species.

Conventional protocols for isolation of plasma (the non-cellular component of blood that remains after removal of cells by centrifugation) involve variable combinations of individual or multiple low/high speed centrifugation steps. In order to assess the contribution of these differential spin steps in the removal of cellular material, we sought to fractionate whole blood from 15 healthy male Caucasian donors (Table S1) through successive centrifugation rounds and investigate the proportion of cell free and cellular miRNAs at each stage (FIG. 1). Samples were initially segregated at a low speed spin to generate plasma (Cloudy Supernatant or "CS") along with three cellular fractions: (1) Red Blood Cells (RBCs or "R"), (2) the Buffy Coat consisting of platelets and White Blood Cells (WBCs or "W") and (3) pure populations of leukocytes isolated by sub-fractionation of blood through Ficoll-Hypaque gradients (Leukocytes or "L"). Since these populations represent the major cellular constituents of blood, we hypothesize them to be the primary contributor of cellular material through either cell carryover or lysis during blood fractionation and collectively define them as contaminant miRNAs. We further segregated the plasma derived cloudy supernatant layer through increasing centrifugal forces into supernatants (S1 and S2) and pellets (P1 and P2) fractions. The supernatant fractions are representative of primarily cell-free circulating RNAs with the pellet fractions characterizing contaminating cellular particles. Amongst the pellet class—the P1 and P2 fractions are distinct in both size and granularity of the isolates. A prominent precipitate is distinguished in the P1 fraction while the P2 fraction has inconsequential cellular particles. All eight fractions (A-H) (FIG. 1) were extracted using Trizol-LS (Invitrogen) and the mirVANA filters (Ambion) and subsequently hybridized to the Affymetrix miRNA arrays. We observe distinct gradients in intensity distributions in all of the 5 plasma derived classes compared to the contaminant miRNAs (FIG. 2A). The graph shows box plots representing background subtracted non-normalized and summarized $\log_2$ intensities of human miRNAs. The result for each fraction is shown on the left with the corresponding background data shown to the right for each fraction. The black bar represents the median of each distribution. The open circles represent the outliers. Fractions isolated with minimal centrifugation (Cloudy supernatant/CS) or hypothesized to be contaminant rich (P1 and P2) display a greater intensity magnitude compared to supernatant fractions of S1 and S2. Taken together these distributions indicate the presence of miRNAs of distinct abundances in the cellular and circulating class and highlights the enrichment of low-abundant species in plasma fractions clarified through successive purification steps.

Correlation of miRNA Intensities Between Individual Fractions and Contaminant Class.

Since the process of sequential centrifugation is hypothesized to result in the segregation of cellular material, we anticipate an increased concentration of contaminant miRNAs in the pellet fraction compared to the clarified supernatant derived from each centrifugation step. Consequently we hypothesize a greater correlation in miRNA populations between the contaminating cellular RNAs and the pellet fraction, compared to the supernatant fractions of S1 and S2. In order to assess the concordance in detected miRNAs between the cellular and each of the plasma derived fractions we first computed the common set of all detected miRNAs in the three contaminant classes. A total of 313 features (Table S2) were identified through a union of WBC, RBC and Leukocytes fractions based on the number of detected features in each fraction assessed through the Wilcoxon-Rank Sum Test (FIG. 2B). These features were then used to compute Spearman rank correlations with the top 100 highest expressing miRNAs derived from the centrifugation of whole blood into 5 plasma-derived fractions (CS, S1, S2, P1 and P2) (FIG. 2C). The contaminant class is designated as LWR and represents 313 miRNAs derived from the union of the Leukocytes, WBC and RBC fractions. Correlation values are shown in the bar scale. We observe a stronger correlation between the CS and P1 fraction with the contaminant list consistent with the hypothesis that these fractions are enriched in cell-associated miRNAs. A reduced correlation is observed for fractions derived from CS (S1, S2 and P2) indicating a progressive clarification of contaminating miRNAs through removal of cellular particles with subsequent centrifugation steps. Interestingly a strong agreement is also observed between S1 and the S1 derived S2 and P2 fractions suggesting that there is no additional advantage in sub-fractionating the S1 sample. Taken together these results indicate that there is a considerable proportion of cellular material that persist in the CS fraction of plasma after the initial spin which can be sufficiently and adequately removed by only one additional low speed centrifugation step. The supernatant fraction (S1), derived after centrifugation display low levels of contaminating miRNAs (FIG. 2C) consequently leading to an enrichment of circulating miRNA species.

Concordance in Expression Levels of Circulating miRNA Species Between the Plasma Derived Classes In order to ensure that sub-fractionation of the CS into the S1 and P1 categories did not results in the loss of true circulating miRNA species, we assessed the concordance in intensities between the CS and ensuing S1 and P1 fractions to determine their extent of similarity. FIGS. 3A-d shows concordance of expression levels of circulating miRNA species between the CS, S1 and P1 fractions. (Spearman Rank Correlation analysis was performed on all detected miRNAs after removal of contaminant features in the 3 samples (CS, S1 and P1). The filtered miRNAs were first stratified into different intensity bins consisting of highest expressing 20, 35, 50, 100 miRNAs based on average intensity levels across all fraction (FIGS. 3A-D) and correlation values calculated for each pair. The correlation values are shown in the bar scale. We observe strong and improved rank order correlations between the CS and S1 fraction (rank correlations >0.6) compared to the CS and pellet (P1) fraction (rank correlations <0.0). This implies that the composition of the S1 and P1 fractions are distinct and consist of unique species of miRNAs. In contrast the strong rank-order correlation between the CS and the S1 class demonstrates the presence of homogenous populations of miRNAs, indicating a preservation of miRNA species between the two plasma fractions through the fractionation process.

Comparison of Expression Levels of Circulating and Cellular miRNAs in the CS and S1 Fractions.

Since the process of sub-fractionation may impact both the integrity and abundance of miRNAs, we wanted to ensure that markers that were conserved between the CS and the S1 fractions did not vary in their expression levels. In order to test this, categories of miRNAs that are common to both these fractions were selected after filtering for contaminants and stratified into different intensity bins consisting of the top 20, 35, 50 or all of the 534 miRNAs (total number of features that remain after removal of 313 contaminant RNAs). We observe no significant difference in the expression level for any of these miRNA classes in either of the supernatant fractions (two sided Student's t-test, with p-values ranging from 0.053 to 0.596) (FIG. 4A). This indicates that most miRNA species remain intact through the separation process from CS to S1. In addition, since the isolation process is predicted to remove contaminant miRNAs we anticipate higher proportions of cellular RNAs in the CS fraction compare to the S1 class. To directly test this we similarly compared expression levels of cellular RNAs stratified into different intensity tiers between the two plasma derived fractions. For all miRNA strata compared, we observe a statistically significant down regulation in abundances for cellular miRNAs in the S1 class with a p-value of 0 (FIG. 4B). This indicates a clarification of these RNAs from the CS to the subsequently derived S1 class as a consequence of the fractionation process. Taken together these result suggests that isolation of the S1 class from the CS minimizes the levels of contaminating cellular RNA, while preserving the expression of circulating miRNA species.

Stability of Expression of Circulating miRNAs Across Biological Replicates.

In principal the process of sub-fractionation, while removing contaminants may potentially impact the stability of expression of the truly circulating miRNA species. In order to assess if the population of miRNAs detected in the CS and S1 fraction display consistent patterns of expression, we investigated the rank order concordance of miRNAs in the CS and S1 fraction across all biological replicates. We hypothesized that conserved and stably expressed miRNAs would have non-stochastic expression levels and hence demonstrate high rank order correlations. In order to test this, miRNAs were selected after filtering out contaminant features and a common set of targets isolated based on average intensities from the CS and S1 fractions across multiple biological replicates. Categories of miRNAs were stratified into intensity bins containing the highest expressing 20, 50, 200 or 543 miRNAs and Spearman Rank Correlation values computed for each category per individual fraction across all samples (FIG. 5A). Our results show modest improvement in the mean correlation values for the CS fractions across the different intensity strata (FIG. 5B). In contrast we observe a statistically significant 2.5 fold increase in correlation in the S1 fraction as the analysis is restricted from the entire 543 features to the highest expressing top 20 miRNA class. (p-value of 9.624552e-18 from two-sided Student's t-test). Taken together this result indicates that the S1 fraction has a stable population of miRNAs that are homogenously expressed across replicates. This fraction hence represents a comprehensive plasma category enriched in circulating markers that can be reproducibly detected in replicate samples.

Variability in Expression of Circulating miRNA Species in Cohorts of Normal Males and Females.

Figure 9:
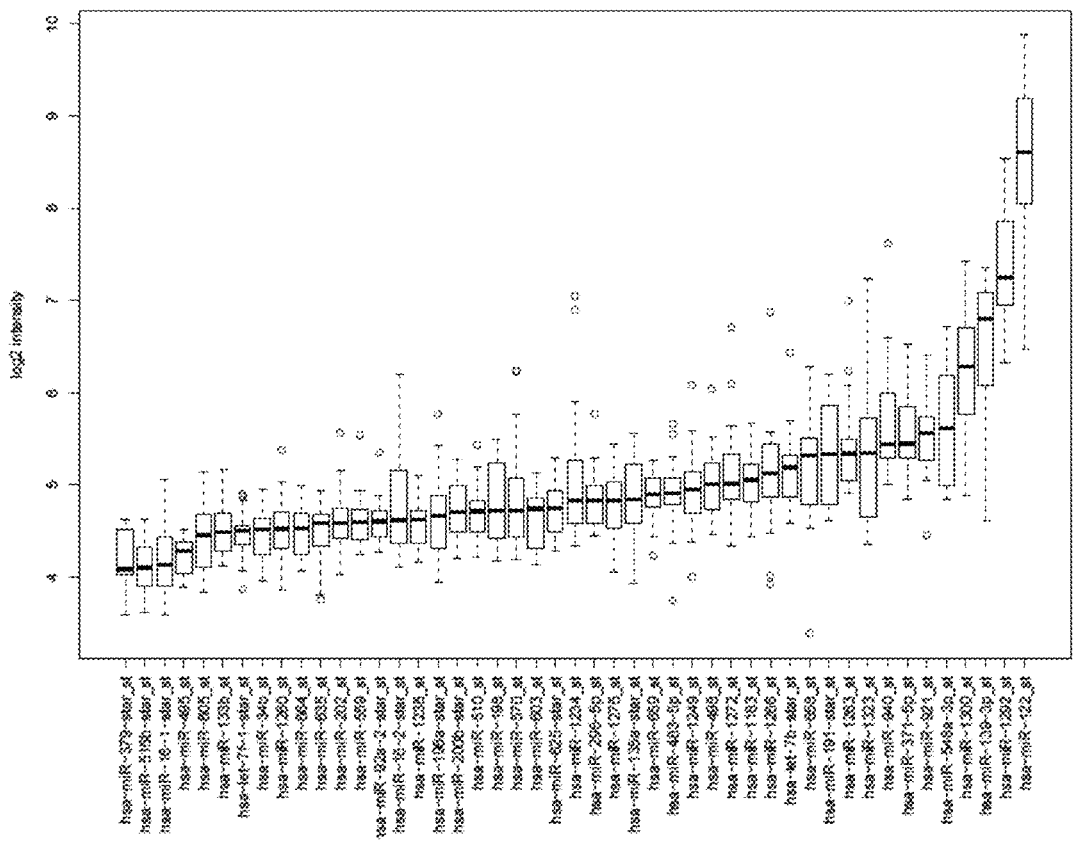
FIG. 9 shows box plots of signal intensity distribution of 47 human miRNAs specific only to circulation (+S/−L) in healthy cohorts of 8 male and 10 female individuals.

The intrinsic variability in expression of a biomarker is a critical determinant for understanding both its normal behavior as well as assessing diseased induced changes. To explore the expression characteristics of circulating miRNAs, we investigated both the intensity and variability of expression of markers isolated from the S1 fraction in cohorts of normal individuals. Samples extracted from 8 males and 10 female Caucasian donors were background adjusted, quantile normalized and the summarized intensities for all microRNA and background probes analyzed (see Table S1 and FIG. S1 in Duttagupta et al. 2011). In order to ensure that markers displaying a wide range of expression values were included in this analysis, individual miRNAs were selected upon presence/absence calls and categorized based on a 50% detection threshold amongst the 18 individuals. Two categories of miRNAs were defined in the S1 fraction: (1) 140 miRNAs present in both circulation (S) and contaminants (L): (+S/+L) and (2) 47 miRNAs present in circulation only: (+S/−L) (See Table 2 (also Table S3 in Duttagupta et al. 2011) and FIG. 9). The variability in each class was assessed through Standard Deviation estimates. We observe a statistically significant reduction in both intensities (p-value of 2.2e-15 from two-sided Students t-test) (FIG. 6A) and standard deviations (p-value of 2.93e-05) (FIG. 6B) in the circulating class (+S/−L) compared to miRNAs that are co-detected both in circulation and contaminants (+S/+L). This result demonstrates that the variability in expression of circulating miRNA species in a population is reduced after removal of contaminating cellular miRNAs. Furthermore, examination of the 47 circulating miRNAs reveal a two fold dynamic range of intensity for this class and reveal candidates that bear evidence of expression derived from tissue of non-hematopoietic origin. Specifically we find hsa-mir-122 to be the highest expressing circulating miRNA in our current dataset with tissue specific expression derived from the liver. Our analysis therefore clearly distinguishes the effects on classification and variability that arise due to varying levels of cellular miRNAs in samples and underscores the importance of isolation practices for the study of circulating species.

Map of Differentially Expressed Gender Specific Circulating miRNAs

Figure 7A:
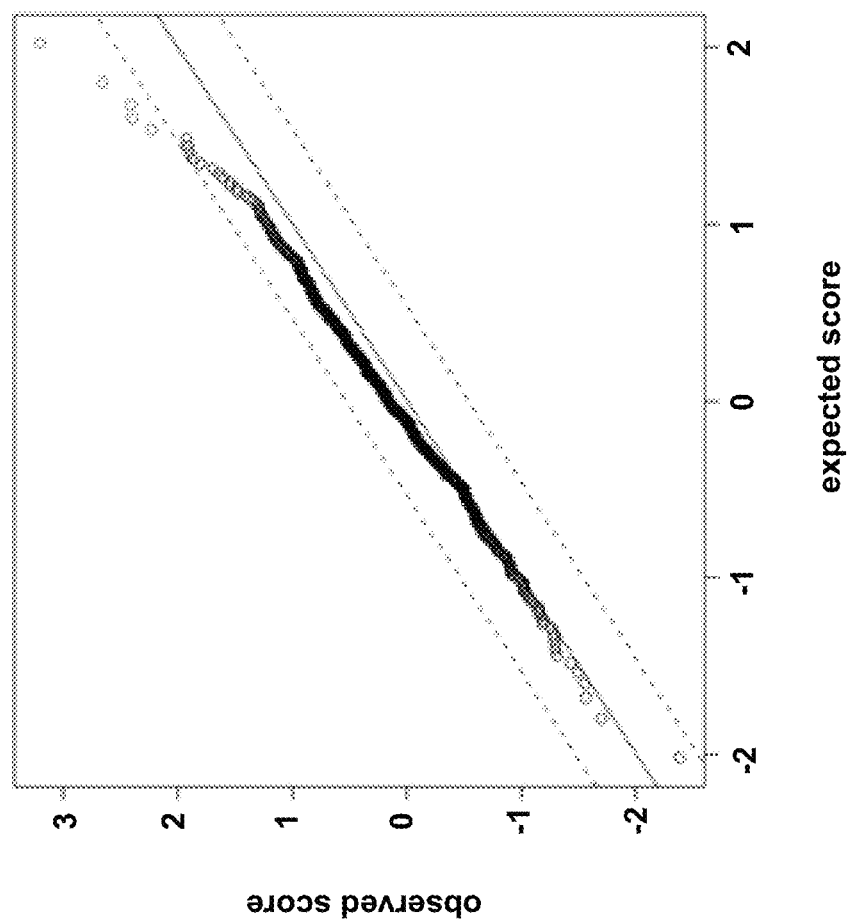
FIG. 7A shows analysis of differentially expressed miRNA species present in gender specific categories as a comparison of observed versus the expected scores obtained by SAM analysis of all 534 features from 8 males and 10 Caucasian females. Each feature is represented by an open circle, and the differentially expressed features represented as red points in the graph. The dashed lines represent a FDR threshold of 5%.
Figure 7B:
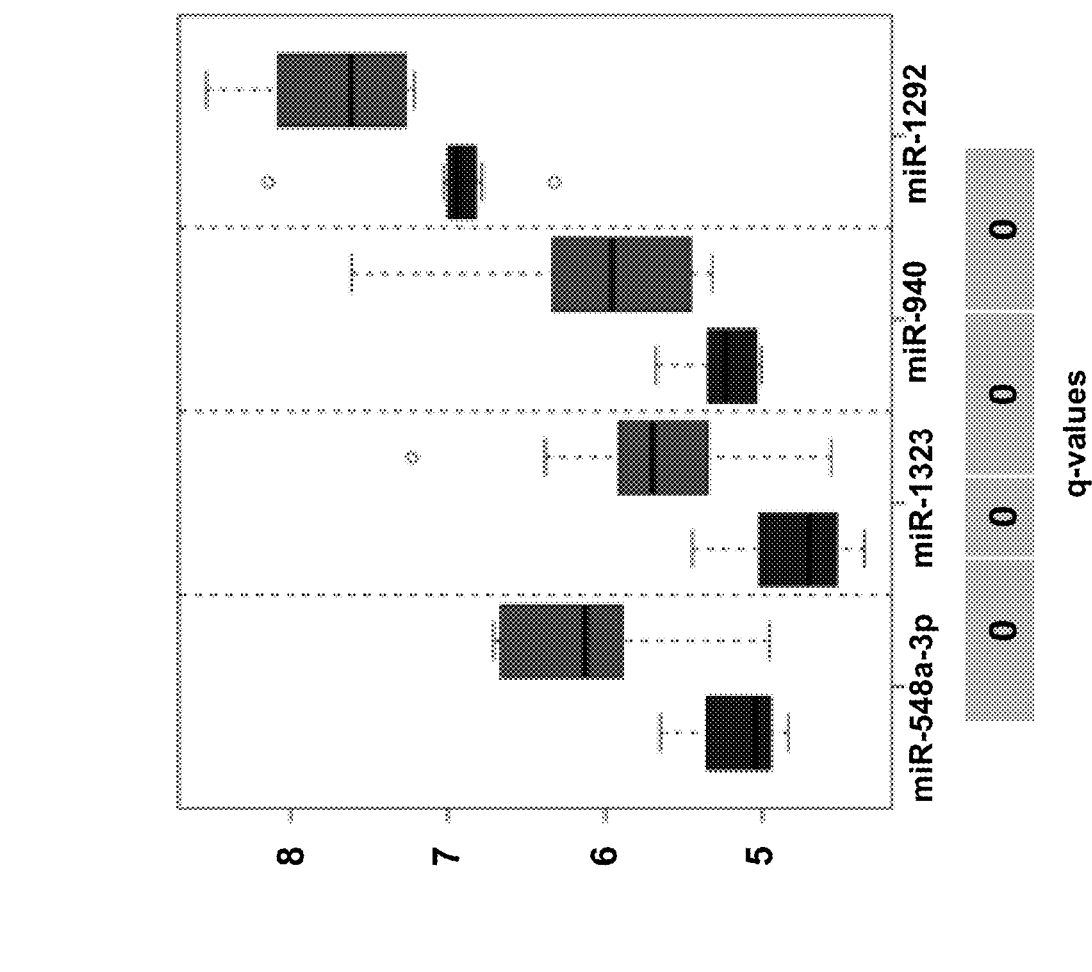
FIG. 7B shows distributions of normalized $\log_2$ signal intensities of 4 differentially expressed features in males (M1-M8; left in each pair) and females (F1-F10; right in each pair).

We next wanted to determine if there were subsets of miRNAs in our dataset that demonstrated gender specific expression in populations of normal male and female individuals. To distinguish this we performed Significance Analysis of Microarrays (SAM) (see Eisen et al. (1998). Proc Natl Acad Sci USA 95: 14863-14868) on the entire collection of 534 miRNAs derived from 8 males and 10 female individuals after removal of contaminant features. We find a total of 5 features to be significantly differentially expressed between males and females at a false discovery rate of 5% (FIG. 7A). Removal of one undetected feature based on Wilcoxon-Rank Sum Test yield a subset of 4 differentially expressed circulating miRNAs present as significant gender-specific discriminators in the individuals studied (FIGS. 7B & C, and FIG. S2 of Duttagupta et al. 2011. Through an analysis of intensity distributions and q-value estimates (see, Storey and Tibshirani (2003). Proc Natl Acad Sci USA 100: 9440-9445), we find all of the 4 miRNAs (hsa-mir-548-3p, hsa-mir-1323, hsa-mir-940 and hsa-mir-1292) to be significantly up regulated in females with a 1.63 to 1.94 fold-change in intensity levels. We did not detect any significantly down regulated miRNAs in this dataset. For all differential expression analyses the q-value estimates were found to be significant and equal to 0 (FIG. 7B) (see, Storey and Tibshirani (2003) Proc Natl Acad Sci USA 100: 9440-9445.). Expression map of these 4 miRNAs through unsupervised hierarchical clustering (FIG. 7C) show a clear separation of the two groups with the exception of 4 female individuals (F1, F3, F5 and F8) indicating thar the miRNA expression profiles between the two groups were significantly different. We observe a strong and uniform expression of all up regulated miRNAs (~log 2 intensity of 6) across most individuals with particularly robust expression observed for hsa-mir-1292 (~log 2 intensity of 7.5) (FIGS. 7B and C). Taken together this data characterizes profiles of differentially regulated circulating miRNAs and reveals distinct gender specific expression patterns for subsets of miRNAs in cohorts of normal male and female individuals.

Methods are disclosed for systematically evaluating the role of heterogeneous cellular miRNAs derived from disparate hematopoietic cells as a pre-analytic variable influencing the isolation and analysis of cell-free circulating miRNAs. Our results show that different fractionation procedures for plasma have varying degrees of efficacy in the removal of red and white blood cells and as a consequence can play a major role in impairing circulating miRNA signatures. Specifically through differential centrifugation of whole blood into distinct classes of supernatants and pellet fractions we show disparate distributions of cellular miRNAs and furthermore demonstrate that the Cloudy Supernatant derived from the first spin is enriched in contaminant miRNAs compared to isolates of subsequent spins (S1 and S2) (FIG. 1). Two lines of evidence support this observation. Firstly, fractionation of the CS isolate leads to a clear separation of signal intensities between the CS derived; S1 and P1 sub-fractions (FIG. 2A). We observe a greater magnitude of signal intensity in the CS and P1 isolates compared to the S1 class, indicative of the presence of higher abundant miRNAs in these fractions. Given the cellular nature of the derivative P1 isolate, we observed that a proportion of high abundant cellular miRNAs persist in the CS fraction that is sequestered in a pellet only as a consequence of additional centrifugation step. (FIG. 2A). Secondly, inter-fraction Pearson correlations analysis conclusively establishes a strong correspondence between the contaminants and the contaminant-rich fractions of CS and P1. This indicates an enrichment of cellular miRNAs in these classes. In contrast a relatively weaker correlation is seen for the S1 and the S1 derived S2 and P2 fractions suggesting that the miRNA signature of this fraction is distinct from the cellular class (FIG. 2C). The results indicate that the P1 and P2 pellet fractions are distinctive, with minimal precipitate observed in the P2 isolate. This indicates that the majority of cellular miRNAs are primarily segregated in the P1 fraction with minimal carryover into the P2 isolate. The residual contaminant species detected in the S1 or S2 fraction is therefore likely to be representative of cellular miRNAs that are present either due to active release from cells of hematopoietic lineage or are derived from haemolyisis of cells during the isolation process.

Figure 3:
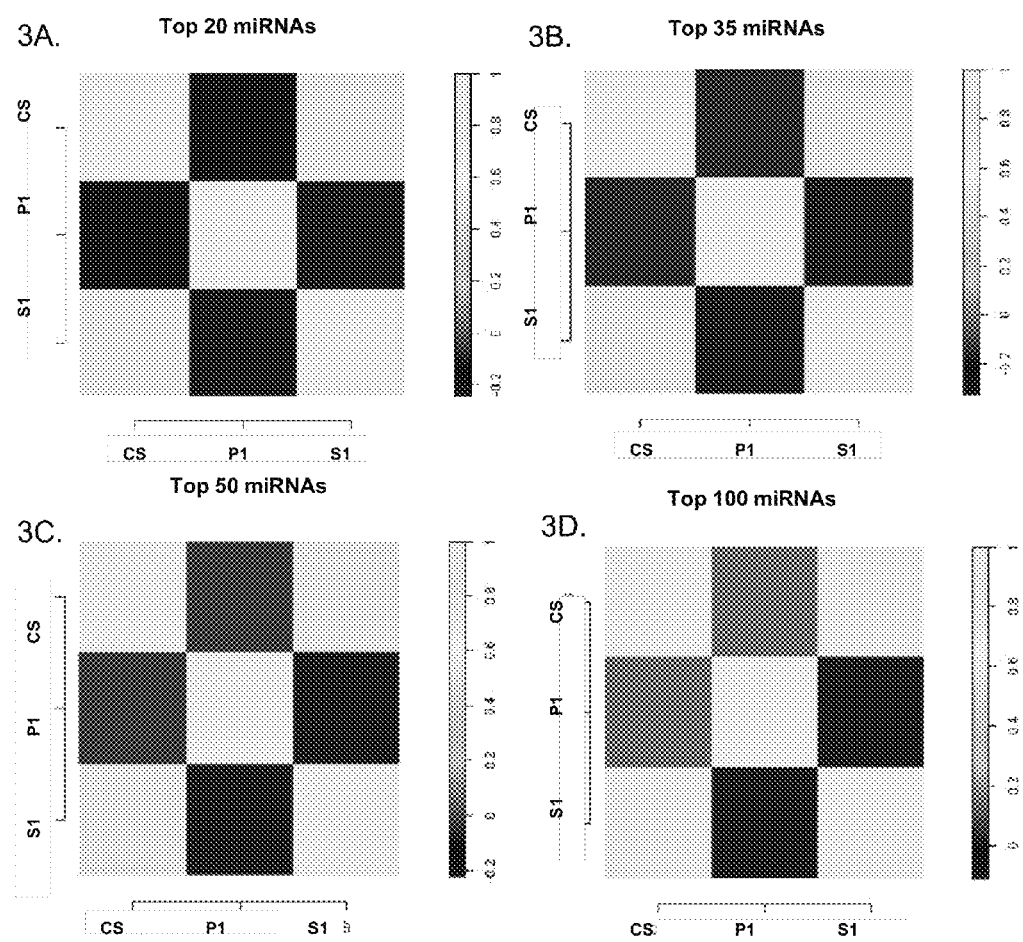
FIG. 3A shows a heat map of Spearman's Rank Correlation coefficients for the highest expressing 20 miRNAs present in CS, P1 and S1 fractions after removal of contaminant features.
FIG. 3B is the same as FIG. 3A but for the highest expressing 35 miRNAs.
FIG. 3C is the same as FIG. 3A but for the highest expressing 50 miRNAs.
FIG. 3D is the same as FIG. 3A but for the highest expressing 100 miRNAs.
Figure 5:
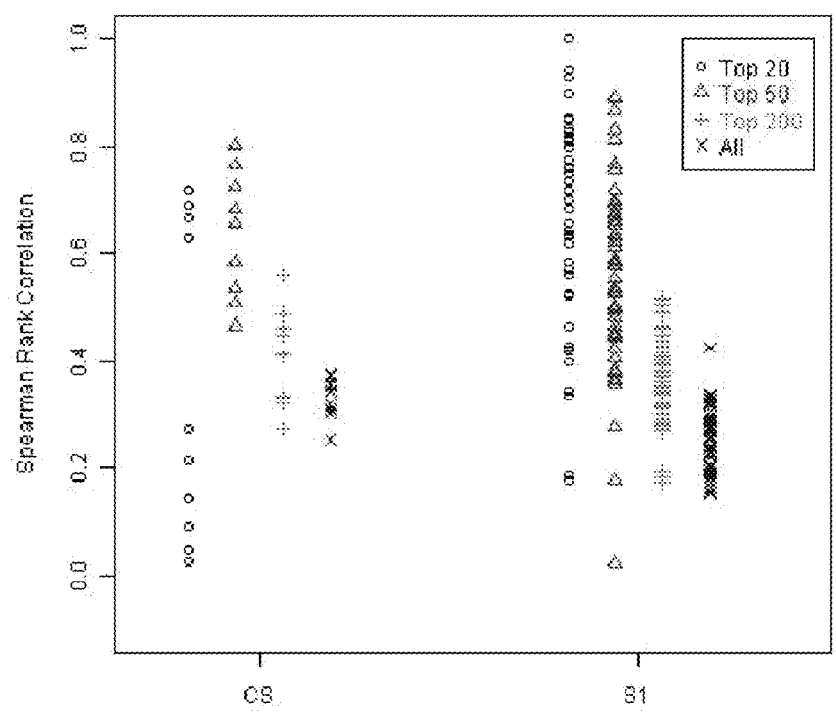
FIG. 5 shows correlation of expression levels of circulating miRNAs across different biological replicates in the CS and S2 fractions.

The high degree of similarity observed between the S1 and S2 isolates (FIG. 2C), suggested that the S1 fraction might have advantages over the Cloudy Supernatant class. The process of removal of contaminating miRNAs from the CS fraction did not lead to the loss of abundance or integrity of the circulating species. We examined the inter-fraction correlations of detected miRNA intensities stratified into different intensity bins and observe a strong correlation between the CS and S1 fraction indicating preservation of circulating species (FIG. 3). No significant difference was observed in intensity distributions between stratified miRNA classes between the CS and S1 fractions supporting the homogeneity of expression of common representative miRNAs between these classes (FIG. 4A). The slightly lower intensities in the S1 fraction are likely due to loss of RNA due to additional extraction steps. This analysis also distinguishes a clear reduction in expression of contaminant miRNAs in the S1 fraction compared to the Cloudy Supernatant class (FIG. 4B). This result conclusively demonstrates that the process of sub-fractionation enhances specificity of circulating markers by removal of cellular miRNA species. Since both the structural and functional integrity of miRNA populations can be influenced by procedural effects, one of the characteristics of specific circulating miRNA markers should be defined by the stability of expression across multiple biological samples. In order to measure reproducibility of expression intensity was examined by stratifying bins of miRNA in the CS, and S1 fractions across multiple replicates through Spearman Rank Correlation Analysis. The results indicate a statistically significant increase in expression levels across different miRNA strata in the S1 compared to the CS fraction, indicating strong consistency in miRNA signatures in the S1 supernatant fraction. FIG. 5 shows Spearman's Rank Correlation coefficients for CS and S1 fractions, across all replicates restricting to the highest expressing 20, 50, 200 or all 534 human miRNAs that are common to the 2 fractions. Each point on the graph represents the rank correlation values across all pair-wise combination of replicates for the category under study. The mean correlation values for the CS and S1 fraction in each intensity strata are as follows: for the CS fraction top 20=0.35, top 50=0.55, top 200=0.4 and all 534=0.33. For the S1 fraction top 20=0.65, top 50=0.55, top 200=0.35 and all 534=0.26.

It is known that the signatures of plasma/serum miRNAs can reflect correlations to physiological or disease conditions (See, Garzon R, Cahn G A, Croce C M (2009) MicroRNAs in Cancer. Annu Rev Med 60: 167-179.). To date 13 types of cancer have been investigated in which expression profiling of circulating miRNAs have revealed both diagnostic and prognostic utility for this class of biomarkers (see Kosaka N, Iguchi H, Ochiya T (2010) Cancer Sci 101: 2087-2092.). Since gene expression as a quantitative phenotype is known to vary within a population, in order to obtain miRNA signatures related to disease classification, it is important to evaluate the range of inter-individual variability across demographic populations. To our knowledge no studies have directly explored this variation in the context of calibrating for contaminant signals. We sought to assess this variability by mapping the circulating miRNA expression profiles from the S1 fraction in healthy population of Caucasian male and female individuals both through Standard Deviation (SD) estimates and Coefficient of Variation (CV) Analysis (data not shown) (FIG. 6). Stratification of miRNAs based on detection in circulation and/or contaminant classes reveal an approximate loss of 66% of all detected miRNAs (93 out of 140 miRNAs that are lost between the +S/−L and the +S/−L classes) through the removal of cellular miRNAs. The proportion of this reduction is comparable to similar extensive overlaps seen between miRNAs signatures derived from plasma and blood (see Storey J D, Tibshirani R (2003). Proc Natl Acad Sci USA 100: 9440-9445) or micro vesicles and peripheral blood mononuclear cells (see, Hunter M P, Ismail N, Zhang X, Aguda B D, Lee E J, et al. (2008) PLoS One 3: e3694.). A direct comparison of the 20 most common circulating miRNAs from healthy individuals over 5 different datasets (reviewed in Reid et al. (2011) Crit Rev Oncol Hematol, November; 80(2):193-208, Epub 2010 Dec. 8 (2010)) reveal, that in agreement to our study at least 70% (14/20) of the reported circulating miRNA species can be mapped to our cellular miRNA signatures (Table 1).

TABLE 1

Overlap of 20 most common circulating miRNAs from healthy individuals and 140 miRNAs present in the +S/+L category.

| 20 common miRNAs * | +S/+L |
|---|---|
| hsa-let-7b | present |
| hsa-miR-16 | present |
| hsa-miR-21 | present |
| hsa-miR-223 | present |
| hsa-miR-24 | present |
| hsa-miR-25 | present |
| hsa-miR-30d | present |
| hsa-miR-320 | absent |
| hsa-miR-106b | present |
| hsa-miR-142-3p | absent |
| hsa-miR-15a | present |
| hsa-miR-183 | absent |
| hsa-miR-186 | absent |
| hsa-miR-19b | present |
| hsa-miR-20a | present |
| hsa-miR-22 | present |
| hsa-miR-26a | present |
| hsa-miR-451 | present |
| hsa-miR-484 | absent |
| hsa-miR-92a | present |

Figure 6A:
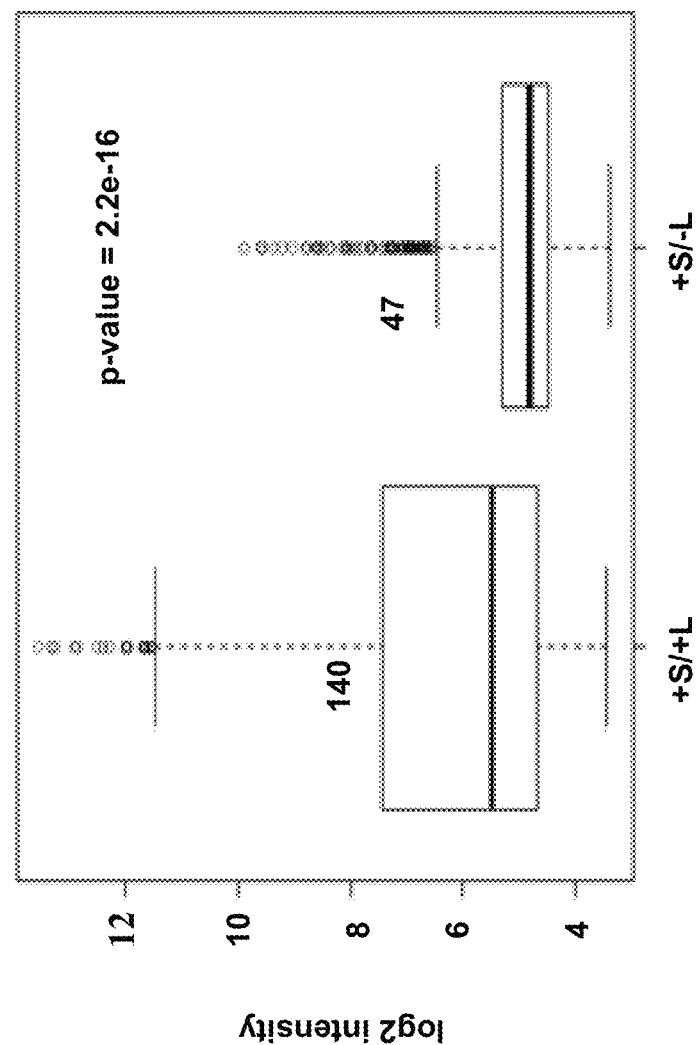
FIG. 6A shows variability of circulating miRNA expression levels in normal cohorts of male and female individuals as box plots of intensity distributions of 140 features common to both circulation and in contaminants (+S/+L) or 47 features specific only to circulation (+S/−L).
Figure 6B:
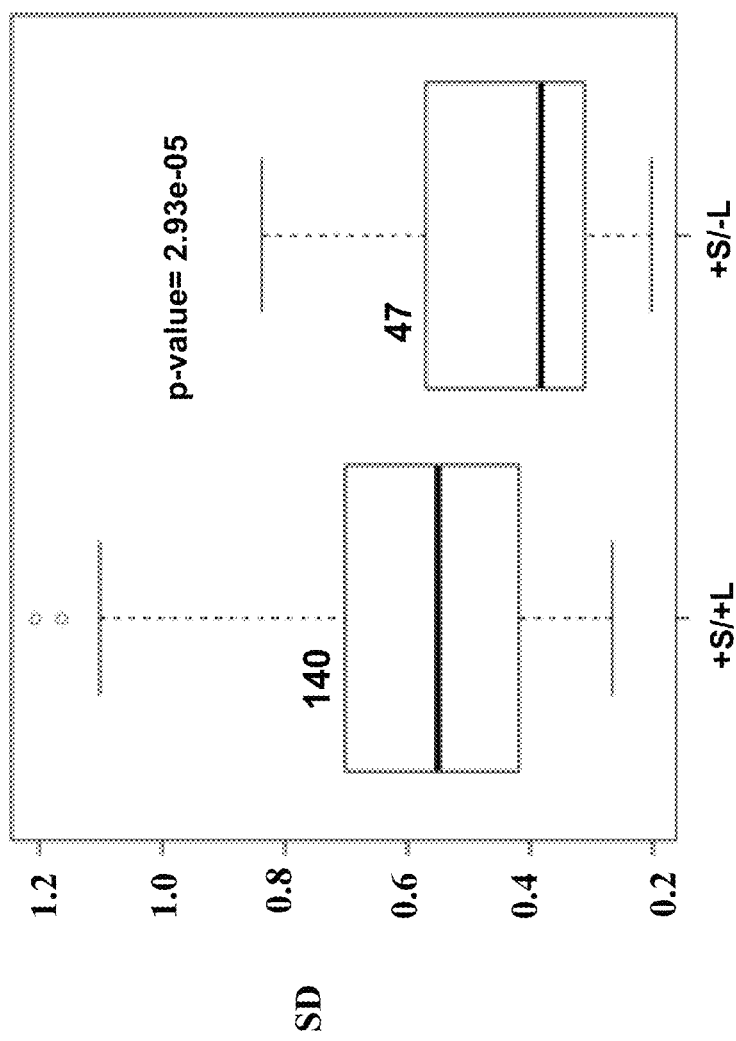
FIG. 6B shows analysis of Coefficient of Variance of these two categories. P-value from two-sided Student's t-test measuring tests of significance is reported.

Markers that are common to both the cellular and circulating categories display a significantly higher variability through both methods of estimates in contrast to miRNAs that are specific only to circulation (FIGS. 6A and B). The black bar represents the median of each distribution. The open circles represent the outliers. This analysis clearly indicates that a considerable proportion of cellular miRNAs persevere in clarified plasma preparation and moreover exhibit significant variability in expression across different individuals in a population. Cumulatively this could be reflective of either varying levels of hematopoietic cell lysis or differences in the proportion of RNA actively released into circulation from hematopoietic cells. Calibration of circulating miRNA signals for specificity though subtraction of these features allows for an improved estimate of intrinsic variability within individuals. Additionally, examination of the relationship of 47 miRNAs in the circulatory class to published lists of circulating miRNAs (see, Tanaka M, et al. (2009) PLoS One 4: e5532) reveal overlaps between the datasets indicating detectability of subsets of these biomarkers across different experimental platforms (Table S3) see Duttagupta et al. 2011. Through literature query and search of two functional databases: microRNA.org and miRNA-Map (see Hsu S D, et al. (2008). Nucleic Acids Res 36: D165-169) we can find additional correspondence to tissue derived expression specificity for a subclass of these RNAs (see, Lee E J, Baek M, Gusev Y, Brackett D J, Nuovo G J, et al. (2008) RNA 14: 35-42. and Landgraf P, Rusu M, Sheridan R, Sewer A, Iovino N, et al. (2007) Cell 129: 1401-1414.) Specifically we can map hsa-mir-122, hsa-mir-495, hsa-34b, hsa-mir-198 and hsa-mir-658 to expression derived from diverse tissues of origins (Table S3), supporting the hypothesis that non-haematopoetically derived miRNAs can enter and persist in circulation.

Gender specific differences are known to play a role not only in the type and susceptibility of diseases but also affect the response to therapeutic treatments (see, Zhang et al. (2009) In Silico Biol 9: 55-63.). In order to assess if the expression of circulating miRNAs demonstrated any gender specificity we sought to explore miRNAs signatures in random cohorts of normal male and female individuals. Through Significance Analysis of Microarrays (SAM) we distinguished 4 circulating miRNAs that are differentially expressed in a gender specific manner. We find all of these miRNAs to be significantly up regulated by 63-95% in females and detect no miRNAs which display a reduction in expression (FIGS. 7B and C). We find correlation of expression of one out of these four miRNAs to sex-specific tissue. Specifically we show that the strong female specific expresser: hsa-mir-940 to be detected in the cervix (see, Lui W et al. (2007) Res 67: 6031-6043.)

A search of Genes-to-Systems Breast Cancer Database we found evidence of interaction of all the 4 miRNAs with gene targets (E2F1, DAPK1 and TIMM50) implicated to be altered in breast cancer cells. (FIG. S3) These results provide functional indications for gender-specific role of these miRNAs. Structurally, a majority of the differentially expressed circulating miRNA species (75%% or 3/4) originate from unannotated intergenic regions with only hsa-mir-1292 mapping to the intron of a gene. Interestingly none of the four miRNAs are found to map to the sex chromosomes. Although the biological roles of these specific miRNAs are obscure, these results provide clear indication for differential expression of circulating miRNAs in a gender specific manner. Additionally, correlation of expression to sex-specific tissues for a subset of these transcripts, provide evidence for a physiological role of these miRNAs in delineating biological differences between the genders.

Several studies have explored the utility and analysis procedures for the study of circulating miRNAs. Although the precise functions and mechanism of action of these RNAs remain undetermined (see Mitchell et al. and Kosaka et al.) accumulating evidence in the form of qPCR and sequencing data (see Garzon et al. and Jima et al.) from a variety of conditions ranging from malignancies to pregnancy (reviewed in Reid et al. 2010) has begun to delineate the diversity of this class of miRNAs as molecular biomarkers correlating expression with physiological states. The current disclosure provides comprehensive global signatures of bona fide circulating miRNA species in the context of cellular miRNA expression in cohorts of normal individuals. By segregating the specificity of measured signals into cell-free and cellular miRNAs the heterogeneity in expression of fluid derived biomarker signatures may be demonstrated. Additionally the data provides categories of miRNAs that can help distinguish circulating miRNAs form cellular counterparts and mitigate the inherent ambiguity in the interpretation of these profiles. As formal recommendations for the study of circulating biomarkers evolve, we anticipate that analysis of circulating miRNAs in such class specific manner would advance both the detection and quantitation strategies utilized for global investigations of miRNA biomarker study.

In another aspect linear acrylamide (LA) may be used as a stabilizer for isolation of circulating miRNA from plasma. Linear Acrylamide is typically used as co precipitant to improve DNA recovery and is a popular reagent as such (see, for example, Gaillard and Strauss (1990) Nucleic Acids Research 18:378 and Wang (2005) J Transl Med. 25(3): 28). LA has not previously been described as a stabilizer for isolation of circulating mirna from plasma. LA may be used to improve recovery from plasma samples that are notoriously rich in RNases with yields that have poor 260/280 absorbance.

LA may be added as a carrier to the plasma samples very early on "before" starting extraction, in an environment that is protein-rich and the nucleic acid fraction is in association with proteins/extracellular bodies. This is a key difference between the way the reagent is used in this application versus as a coprecipitant during ethanol extraction (where the nucleic acid is already in solution).

Mechanistically LA may be acting as nucleation points to aggregate nucleic acids and hence slow down the catalytic activity of RNases. Different types of carriers were tested, for example, different non-human non-coding RNAs i.e t-RNA, bac—RNA etc) and they all improve the integrity of the recovered RNA but confound the yields. LA is a nice alternative as it has no contribution to yield but has a positive impact on RNA integrity.

Fractionation of plasma from whole blood and isolation of miRNA. Whole Blood was collected through informed consent from healthy male and female Caucasian donors, age matched within 25 years in Sodium EDTA tubes from the Stanford Blood Center see Table S1 in Duttagupta et al. 2011. The samples were stored on ice and processed within 4 hours of draw. All centrifugation steps were performed at 4° C. All samples were initially spun at 1700 g for 10 minutes to separate the plasma from the Buffy Coat and Red Blood Cells. Leukocytes were separately isolated from whole blood stabilized with yeast tRNA (Ambion) and fractionated through Ficoll-Hypaque gradients. The plasma (designated as the Cloudy Supernatant) was then re-centrifuged at 2000 g for 10 minutes to obtain the Supernatant 1 (S1) and Pellet 1 (P1) fractions. For the fractionation studies the S1 fraction was additionally centrifuged at 12000 g for 10 minutes to generate the Supernatant 2 (S2) and Pellet 2 (P2) fractions. All the pellet fractions were washed once with 1×PBS and then reconstituted in 0.5 ml×PBS. Similarly the Red Blood Cell fraction was washed twice with 3× volumes of 1×PBS and the pellet collected. To all fractions 3 volumes of Trizol-LS reagent (Invitrogen) and 10 ug/mL of Yeast Total Carrier RNA (Ambion) were added to stabilize the samples. Samples were isolated through multiple organic extractions using 0.3 volume of chloroform followed by phenol chloroform extractions. Total RNA including miRNA was purified from the aqueous phase using 1.25 volume of ethanol and eluted through the mirVANA columns (Ambion).

Labeling and hybridization of plasma samples to the Affymetrix miRNA Array. Total RNA ranging in concentration from 200-1000 ng were labeled using the Genisphere HSR labeling kit (P/N HSR30FTA) and hybridized overnight to the Affymetrix Genechip miRNA array (P/N 901326). The arrays were washed and stained using standard Affymetrix protocols and scanned using the Affymetrix GCS 3000 7G Scanner. Feature intensities were extracted using the miRNA_1-0_2×gain library files.

Analysis of the miRNA data and Data Preprocessing. The workflow for data preprocessing consisted of extraction of intensities for each individual feature followed by detection calls based on Wilcoxon Rank Sum test, background subtraction based on GC content of anti-genomic probes, transformation of values through addition of a small constant (value 16), quantile normalization and finally median summarization of all probe sets for each feature. The detection and background adjustment were done via Affymetrix miRNA QC Tool and the rest of workflow was performed under R programming environment, available at the r-project.org web site (see, Ihaka R G R (1996) J Comput Graphical Stat 1996 5: 299-314.). All reported intensity data are $\log_2$ transformed. All p-values are calculated by two-sided Student's t-test. The data discussed in this manuscript has been deposited in NCBI's Gene Expression Omnibus and will be accessible through GEO Series accession number upon curation.

Generation of Contaminant Features List.

For determining the list of miRNAs that were present in the contamination class, we first determined the number of detected miRNAs in each of the 3 contaminant categories of Red Blood Cells (RBC), White Blood Cells (WBC) and Leukocytes. A 100% detection criterion (i.e present in all of the samples in each category) was applied for selecting individual miRNAs. A union of all the miRNAs present in these three classes was then taken to obtain 313 miRNAs that are co-detected in all these 3 contaminant classes see Table S2 in Duttagupta et al. 2011.

Analysis of Fractionation Data.

For comparison of signal distributions (FIG. 2A) and rank correlations (FIGS. 2C, 3, 4, 5) between different plasma (CS, S1, S2, P1 and P2) and cellular categories (L, W, R), non-normalized data from each fraction was analyzed to preserve the individual distributions. For inter and intra-fraction correlation analysis the average intensities for all the 847 human miRNAs (FIG. 2C) or 534 human miRNAs that can be counted after removal of contaminant features (FIGS. 3, 4, 5) were first computed across all samples within an individual fraction under study. The average intensities were then sorted and miRNAs binned into different intensity strata. Spearman rank correlation coefficients were calculated for a given set of features in each intensity bin for comparison between or within a particular set of fractions.

Analysis of Variability Data.

For exploration of inter-individual variability in healthy cohorts of 8 males and 10 females, all individual samples were quantile normalized together and the numbers of detected miRNAs selected based on the Wilcoxon-Rank Sum test. Features were then filtered for contaminant miRNAs and counted based on a 50% detection threshold for the population under study (i.e. present in at least 9 out of the 18 individuals. Subsequently, selected miRNAs were stratified into 2 classes based on presence (+) or absence (−) of detected features in contaminants (L) or circulation (S). The number of miRNAs in the two categories selected were: (a) +S/+L: with 140 features and (b) +S/−L: with 47 features. For each of these classes, intensity and variability was measured including intensities from all individuals. Variability estimates were done through either standard deviation estimates (FIG. 6) or coefficient of variation analysis (data not shown).

Gender Specific Differential Expression and Hierarchical Clustering of Intensity Data.

Figure 7C:
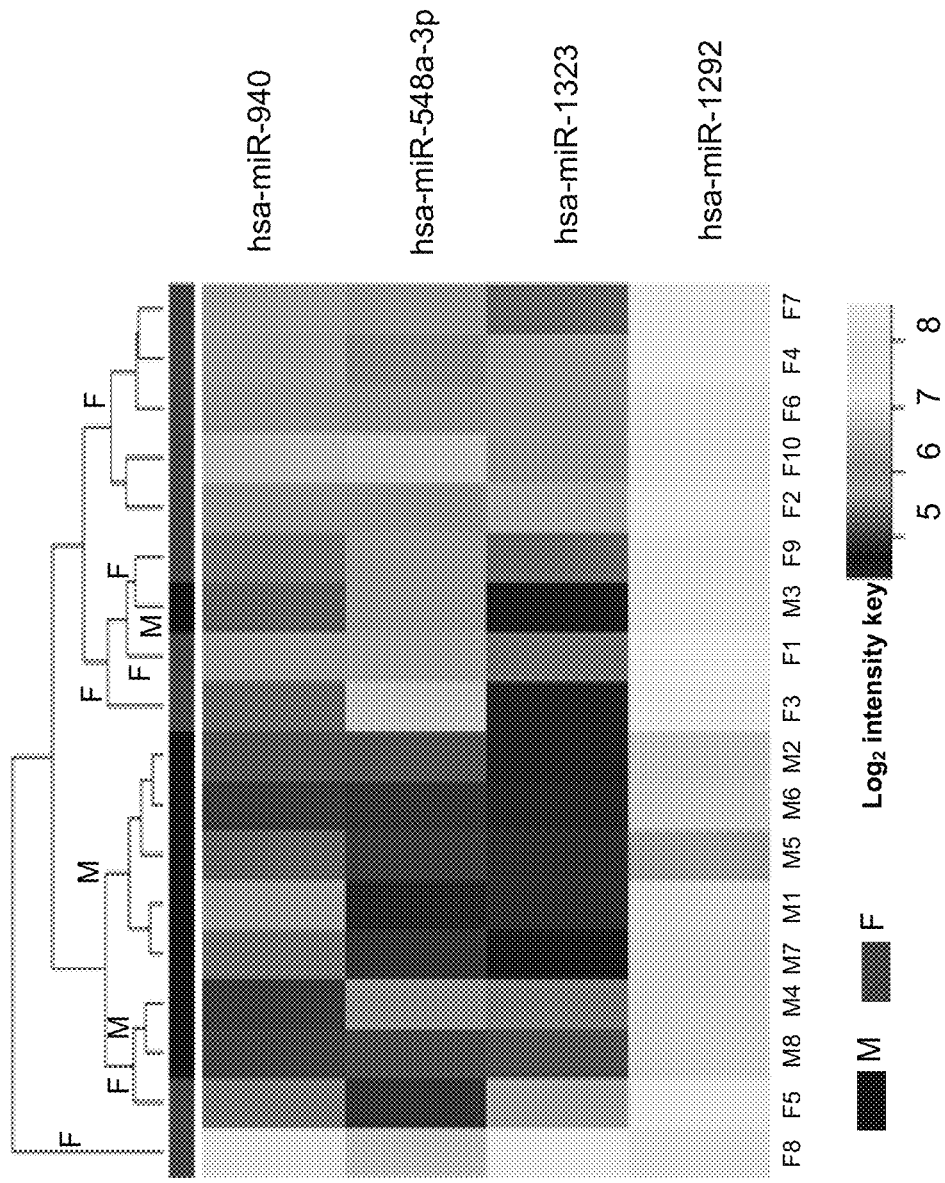
FIG. 7C shows hierarchical clustering of samples (males indicated by M: M1-M8 and females indicated by F: F1-F10) based on summarized intensity values from the 4 differentially expressed circulating miRNAs. The $\log_2$ intensity values are shown in the bar scale.

For exploration of gender specific differential expression, normalized summarized intensities from 8 males and 10 females were analyzed using Significance Analysis of Microarray data (SAM). (See, Tusher V G, Tibshirani R, Chu G (2001) Proc Natl Acad Sci USA 98: 5116-5121.) All 534 features were included in this analysis after removal of contaminant miRNAs and features with significant differential expression levels (DE) detected at a false discovery rate (FDR) of 5%. Expected scores were calculated though 1000 permutations in SAM. A total of 5 DE features were determined which were subsequently filtered for detection calls and miRNAs not detected in any samples were removed. (FIG. 7A). This process resulted in the elimination of hsa-miR-1181. From this analysis a total of 4 up regulated features were distinguished in females (FIG. 7B) see Duttagupta et al. 2011. and were further selected for clustering to delineate relationships between the two sexes. The unsupervised Hierarchical clustering algorithm in the R "hclust" function was used with Euclidean distance matrix and complete-linkage agglomeration. The heat map was generated by the R "gplots" package (FIG. 7C). All gender specific features were mapped to the April 2010 mirBASE release 16 to get chromosomal and genomic locations.

From the foregoing it can be seen that the present invention provides a flexible and scalable method for analysis. All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims. Table 2 lists miRNAs unique to circulation +S/−L (type 1) and miRNAs common to cellular and circulation +S/+L (type 2). ND is not determined tissue of origin.

TABLE 2

| Feature | Type | total #present | Tissue of Origin * |
|---|---|---|---|
| hsa-let-7b-star_st | 1 | 18 | ND |
| hsa-let-7f-1-star_st | 1 | 11 | ND |
| hsa-miR-198_st | 1 | 12 | prostate |
| hsa-miR-139-3p_st | 1 | 18 | ND |
| hsa-miR-122_st | 1 | 18 | liver |
| hsa-miR-34b_st | 1 | 9 | Trachaea, Lung, Ovary, Testis |
| hsa-miR-296-5p_st | 1 | 12 | ND |
| hsa-miR-371-5p_st | 1 | 18 | ND |
| hsa-miR-133b_st | 1 | 14 | ND |
| hsa-miR-483-5p_st | 1 | 17 | ND |
| hsa-miR-202_st | 1 | 12 | Testis |
| hsa-miR-495_st | 1 | 9 | Placenta |
| hsa-miR-498_st | 1 | 17 | ND |
| hsa-miR-510_st | 1 | 15 | Testis |
| hsa-miR-559_st | 1 | 17 | ND |
| hsa-miR-570_st | 1 | 18 | ND |
| hsa-miR-548a-3p_st | 1 | 18 | ND |
| hsa-miR-603_st | 1 | 12 | ND |
| hsa-miR-605_st | 1 | 10 | ND |
| hsa-miR-635_st | 1 | 10 | ND |
| hsa-miR-658_st | 1 | 13 | Prostate |
| hsa-miR-659_st | 1 | 15 | ND |
| hsa-miR-1323_st | 1 | 18 | ND |
| hsa-miR-921_st | 1 | 18 | ND |
| hsa-miR-940_st | 1 | 14 | ND |
| hsa-miR-1183_st | 1 | 14 | ND |
| hsa-miR-1234_st | 1 | 12 | ND |

TABLE 2-continued

| Feature | Type | total #present | Tissue of Origin * |
|---|---|---|---|
| hsa-miR-1238_st | 1 | 10 | ND |
| hsa-miR-1300_st | 1 | 18 | ND |
| hsa-miR-1249_st | 1 | 14 | ND |
| hsa-miR-1260_st | 1 | 10 | ND |
| hsa-miR-1263_st | 1 | 18 | ND |
| hsa-miR-1266_st | 1 | 15 | ND |
| hsa-miR-1272_st | 1 | 18 | ND |
| hsa-miR-1276_st | 1 | 17 | ND |
| hsa-miR-1292_st | 1 | 18 | ND |
| hsa-miR-664_st | 1 | 11 | ND |
| hsa-miR-16-1-star_st | 1 | 9 | ND |
| hsa-miR-92a-2-star_st | 1 | 12 | ND |
| hsa-miR-16-2-star_st | 1 | 14 | ND |
| hsa-miR-196a-star_st | 1 | 11 | ND |
| hsa-miR-200b-star_st | 1 | 13 | ND |
| hsa-miR-135a-star_st | 1 | 16 | ND |
| hsa-miR-191-star_st | 1 | 17 | ND |
| hsa-miR-379-star_st | 1 | 11 | ND |
| hsa-miR-516b-star_st | 1 | 10 | ND |
| hsa-miR-625-star_st | 1 | 15 | ND |
| hsa-let-7a_st | 2 | 18 | |
| hsa-let-7b_st | 2 | 18 | |
| hsa-let-7c_st | 2 | 18 | |
| hsa-let-7d_st | 2 | 18 | |
| hsa-let-7e_st | 2 | 12 | |
| hsa-let-7f_st | 2 | 14 | |
| hsa-let-7g_st | 2 | 18 | |
| hsa-let-7i_st | 2 | 18 | |
| hsa-miR-15a_st | 2 | 16 | |
| hsa-miR-16_st | 2 | 18 | |
| hsa-miR-17_st | 2 | 18 | |
| hsa-miR-18a_st | 2 | 16 | |
| hsa-miR-19a_st | 2 | 11 | |
| hsa-miR-19b_st | 2 | 18 | |
| hsa-miR-20a_st | 2 | 18 | |
| hsa-miR-21_st | 2 | 11 | |
| hsa-miR-22_st | 2 | 16 | |
| hsa-miR-23a_st | 2 | 18 | |
| hsa-miR-24_st | 2 | 18 | |
| hsa-miR-25_st | 2 | 18 | |
| hsa-miR-26a_st | 2 | 18 | |
| hsa-miR-27a_st | 2 | 17 | |
| hsa-miR-29a_st | 2 | 15 | |
| hsa-miR-30a_st | 2 | 11 | |
| hsa-miR-92a_st | 2 | 18 | |
| hsa-miR-93_st | 2 | 18 | |
| hsa-miR-99a_st | 2 | 10 | |
| hsa-miR-103_st | 2 | 18 | |
| hsa-miR-106a_st | 2 | 18 | |
| hsa-miR-107_st | 2 | 18 | |
| hsa-miR-192_st | 2 | 15 | |
| hsa-miR-197_st | 2 | 9 | |
| hsa-miR-199a-5p_st | 2 | 12 | |
| hsa-miR-199a-3p_st | 2 | 15 | |
| hsa-miR-30c_st | 2 | 13 | |
| hsa-miR-30d_st | 2 | 17 | |
| hsa-miR-181a_st | 2 | 15 | |
| hsa-miR-182_st | 2 | 17 | |
| hsa-miR-199b-3p_st | 2 | 17 | |
| hsa-miR-210_st | 2 | 10 | |
| hsa-miR-221_st | 2 | 17 | |
| hsa-miR-222_st | 2 | 17 | |
| hsa-miR-223_st | 2 | 18 | |
| hsa-miR-15b_st | 2 | 18 | |
| hsa-miR-23b_st | 2 | 18 | |
| hsa-miR-27b_st | 2 | 11 | |
| hsa-miR-30b_st | 2 | 14 | |
| hsa-miR-125b_st | 2 | 9 | |
| hsa-miR-130a_st | 2 | 18 | |
| hsa-miR-140-3p_st | 2 | 18 | |
| hsa-miR-143_st | 2 | 10 | |
| hsa-miR-145_st | 2 | 13 | |
| hsa-miR-191_st | 2 | 18 | |
| hsa-miR-125a-5p_st | 2 | 12 | |
| hsa-miR-125a-3p_st | 2 | 14 | |
| hsa-miR-126_st | 2 | 18 | |
| hsa-miR-146a_st | 2 | 17 | |

TABLE 2-continued

| Feature | Type | total #present | Tissue of Origin * |
|---|---|---|---|
| hsa-miR-150_st | 2 | 17 | |
| hsa-miR-185_st | 2 | 18 | |
| hsa-miR-194_st | 2 | 14 | |
| hsa-miR-320a_st | 2 | 18 | |
| hsa-miR-155_st | 2 | 12 | |
| hsa-miR-106b_st | 2 | 18 | |
| hsa-miR-299-3p_st | 2 | 17 | |
| hsa-miR-296-3p_st | 2 | 18 | |
| hsa-miR-130b_st | 2 | 18 | |
| hsa-miR-30e_st | 2 | 12 | |
| hsa-miR-361-5p_st | 2 | 15 | |
| hsa-miR-361-3p_st | 2 | 9 | |
| hsa-miR-363_st | 2 | 13 | |
| hsa-miR-370_st | 2 | 15 | |
| hsa-miR-378_st | 2 | 10 | |
| hsa-miR-330-3p_st | 2 | 17 | |
| hsa-miR-342-3p_st | 2 | 18 | |
| hsa-miR-337-3p_st | 2 | 18 | |
| hsa-miR-151-5p_st | 2 | 18 | |
| hsa-miR-151-3p_st | 2 | 15 | |
| hsa-miR-324-3p_st | 2 | 14 | |
| hsa-miR-335_st | 2 | 9 | |
| hsa-miR-423-5p_st | 2 | 9 | |
| hsa-miR-423-3p_st | 2 | 10 | |
| hsa-miR-425_st | 2 | 18 | |
| hsa-miR-18b_st | 2 | 12 | |
| hsa-miR-20b_st | 2 | 18 | |
| hsa-miR-451_st | 2 | 18 | |
| hsa-miR-409-3p_st | 2 | 12 | |
| hsa-miR-486-5p_st | 2 | 18 | |
| hsa-miR-432_st | 2 | 18 | |
| hsa-miR-193b_st | 2 | 9 | |
| hsa-miR-181d_st | 2 | 11 | |
| hsa-miR-500_st | 2 | 10 | |
| hsa-miR-532-5p_st | 2 | 10 | |
| hsa-miR-455-3p_st | 2 | 18 | |
| hsa-miR-92b_st | 2 | 9 | |
| hsa-miR-584_st | 2 | 10 | |
| hsa-miR-589_st | 2 | 14 | |
| hsa-miR-628-5p_st | 2 | 14 | |
| hsa-miR-638_st | 2 | 18 | |
| hsa-miR-652_st | 2 | 13 | |
| hsa-miR-663_st | 2 | 16 | |
| hsa-miR-654-3p_st | 2 | 15 | |
| hsa-miR-660_st | 2 | 16 | |
| hsa-miR-320b_st | 2 | 18 | |
| hsa-miR-320c_st | 2 | 18 | |
| hsa-miR-744_st | 2 | 11 | |
| hsa-miR-885-5p_st | 2 | 10 | |
| hsa-miR-877_st | 2 | 18 | |
| hsa-miR-665_st | 2 | 13 | |
| hsa-miR-923_st | 2 | 18 | |
| hsa-miR-933_st | 2 | 10 | |
| hsa-miR-938_st | 2 | 12 | |
| hsa-miR-939_st | 2 | 18 | |
| hsa-miR-1182_st | 2 | 18 | |
| hsa-miR-1225-5p_st | 2 | 12 | |
| hsa-miR-1228_st | 2 | 18 | |
| hsa-miR-1207-5p_st | 2 | 18 | |
| hsa-miR-1246_st | 2 | 18 | |
| hsa-miR-1254_st | 2 | 18 | |
| hsa-miR-1267_st | 2 | 18 | |
| hsa-miR-1268_st | 2 | 16 | |
| hsa-miR-1275_st | 2 | 15 | |
| hsa-miR-1281_st | 2 | 18 | |
| hsa-miR-1280_st | 2 | 17 | |
| hsa-miR-1308_st | 2 | 17 | |
| hsa-miR-320d_st | 2 | 18 | |
| hsa-miR-1825_st | 2 | 17 | |
| hsa-miR-1826_st | 2 | 18 | |
| hsa-miR-18a-star_st | 2 | 11 | |
| hsa-miR-23a-star_st | 2 | 15 | |
| hsa-miR-221-star_st | 2 | 11 | |
| hsa-miR-138-1-star_st | 2 | 18 | |
| hsa-miR-149-star_st | 2 | 18 | |
| hsa-miR-150-star_st | 2 | 16 | |
| hsa-miR-106b-star_st | 2 | 11 | |
| hsa-miR-30c-1-star_st | 2 | 14 | |
| hsa-miR-425-star_st | 2 | 16 | |
| hsa-miR-551b-star_st | 2 | 18 | |
| hsa-miR-589-star_st | 2 | 13 | |
| hsa-miR-550-star_st | 2 | 9 | |
| hsa-miR-1228-star_st | 2 | 18 | |

What is claimed is:

1. A method for analyzing circulating miRNAs within a sample of blood comprising segregating the circulating miRNAs from cell-associated miRNAs by: (a) spinning the sample of blood to separate it into a cloudy supernatant fraction of plasma, a white blood cell fraction and a red blood cell fraction; (b) removing cell-associated RNAs from the cloudy supernatant fraction by spinning the cloudy supernatant fraction to separate it into a first supernatant primarily including cell-free circulating miRNAs and a first pellet enriched in cell-associated miRNAs; (c) optionally spinning the first supernatant to separate it into a second supernatant primarily including cell-free circulating miRNAs and a second pellet enriched in cell-associated miRNAs; (d) extracting total RNA from either the first supernatant, if step (c) has not been performed, or the second supernatant if step (c) has been performed, wherein the resulting total RNA is enriched in circulating miRNAs as compared to
the starting blood sample, wherein the spin of step (a) is at about 1700 g for 10 minutes and the spin of step (b) is at about 2000 g for 10 minutes and the spin of step (c) is at about 12000 g for 10 minutes;
analyzing the total RNA for circulating miRNA content; and
extracting out interfering signals from contaminant cells in the total RNA, wherein the extracting is performed by a computer upon data comprising the interfering signals from the contaminant cells and signals from the circulating miRNA content, wherein the extracting comprises background subtraction based on GC content of anti-genomic probes.

2. The method of claim 1 wherein the step of analyzing is hybridizing the total RNA to an array comprising probes complementary to miRNA.

3. The method of claim 1 wherein the step of analyzing is qPCR of the total RNA to determine circulating miRNA content.

4. The method of claim 1 wherein the step of analyzing is sequencing of the total RNA to determine circulating miRNA content.

5. The method of claim 1 wherein a stabilizer is added before the total RNA is extracted.

6. The method of claim 5 wherein the stabilizer comprises linear acrylamide.

7. The method of claim 5 wherein the stabilizer comprises a non-human RNA supplement, and wherein the non-human RNA supplement is yeast RNA.

8. The method of claim 5 wherein the stabilizer comprises Trizol-LS.

9. The method of claim 1, wherein the extracting further comprises:
detecting intensities for the interfering signals and intensities for the signals from the circulating miRNA content by the computer; and filtering out data for the detected intensities for the interfering signals by the computer.

10. The method of claim 1, wherein the extracting further comprises at least one of, data transformation, quantile normalization, and median summarization of the data comprising the interfering signals from the contaminant cells and the signals from the circulating miRNA content.

\* \* \* \* \*